(12) United States Patent
McCormick et al.

(10) Patent No.: US 10,201,589 B2
(45) Date of Patent: Feb. 12, 2019

(54) **COMPOSITIONS AND METHODS FOR TREATING DISEASE USING *SALMONELLA* T3SS EFFECTOR PROTEIN (SIPA)**

(71) Applicant: UNIVERSITY OF MASSACHUSETTS, Boston, MA (US)

(72) Inventors: Beth McCormick, Haverhill, MS (US); Regino Mercado-Lubo, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/103,844

(22) PCT Filed: Dec. 11, 2014

(86) PCT No.: PCT/US2014/069707
§ 371 (c)(1),
(2) Date: Jun. 10, 2016

(87) PCT Pub. No.: WO2015/089268
PCT Pub. Date: Jun. 18, 2015

(65) Prior Publication Data
US 2017/0035837 A1 Feb. 9, 2017

Related U.S. Application Data

(60) Provisional application No. 61/914,600, filed on Dec. 11, 2013.

(51) Int. Cl.
| | | |
|---|---|---|
| A61K 38/00 | (2006.01) | |
| A61K 38/16 | (2006.01) | |
| A61K 47/48 | (2006.01) | |
| A61K 45/06 | (2006.01) | |

(52) U.S. Cl.
CPC ............ *A61K 38/164* (2013.01); *A61K 45/06* (2013.01); *A61K 47/48023* (2013.01); *A61K 47/48038* (2013.01); *A61K 47/48246* (2013.01); *A61K 47/48415* (2013.01); *A61K 47/48861* (2013.01)

(58) Field of Classification Search
None
See application file for complete search history.

(56) References Cited

U.S. PATENT DOCUMENTS

| | | | |
|---|---|---|---|
| 3,859,277 A | 1/1975 | Murakami et al. | 540/527 |
| 4,039,578 A | 8/1977 | Suami | 564/33 |
| 4,150,149 A | 4/1979 | Wolfsen | 436/542 |
| 4,301,277 A | 11/1981 | Acton et al. | 536/6.4 |
| 4,314,054 A | 2/1982 | Acton et al. | 536/6.4 |
| 4,361,544 A | 11/1982 | Goldenberg | 424/1.49 |
| 4,444,744 A | 4/1984 | Goldenberg | 424/1.49 |
| 4,490,529 A | 12/1984 | Rosowsky | 544/260 |
| 4,585,859 A | 4/1986 | Mosher et al. | 536/6.4 |
| 4,725,687 A | 2/1988 | Piper et al. | 544/279 |
| 4,902,791 A | 2/1990 | Roger et al. | 536/17.7 |
| 4,990,538 A | 2/1991 | Harris et al. | 514/648 |
| 5,004,606 A | 4/1991 | Frincke et al. | 424/178.1 |
| 5,429,824 A | 7/1995 | June | 424/489 |
| 5,503,723 A | 4/1996 | Ruddy et al. | 204/450 |
| 5,700,649 A | 12/1997 | Morton et al. | 435/7.1 |
| 5,718,919 A | 2/1998 | Ruddy et al. | 424/489 |
| 5,851,789 A | 12/1998 | Simon et al. | 435/32 |
| 5,993,828 A | 11/1999 | Morton | 424/277.1 |
| 6,238,878 B1 | 5/2001 | Jakobsen et al. | 435/13 |
| 6,632,979 B2 | 10/2003 | Erickson et al. | 800/18 |
| 6,664,386 B1 * | 12/2003 | Galan | C12N 15/74 435/320.1 |
| 6,905,839 B2 | 6/2005 | Furuta | 435/29 |
| 7,348,030 B1 | 3/2008 | Sung et al. | 424/491 |
| 7,387,790 B2 | 6/2008 | Shorr et al. | 424/450 |
| 7,550,282 B2 | 6/2009 | Margel et al. | 435/219 |
| 7,550,441 B2 | 6/2009 | Farokhzad et al. | 514/44 R |
| 7,563,457 B2 | 7/2009 | Cha et al. | 424/491 |

(Continued)

FOREIGN PATENT DOCUMENTS

| | | |
|---|---|---|
| DE | 267495 | 5/1989 |
| EP | A 0142220 | 5/1985 |

(Continued)

OTHER PUBLICATIONS

Wall et al. 2010 (Targeting Tumors with *Salmonella Typhimurium*—Potential for Therapy; Oncotarget 1: 721-728).*
Wall et al. 2007 (Identification of the *Salmonella enterica* serotype Typhimurium SiipA domain responsible for inducing neutrophil recruitment across the intestinal epithelium; Cellular Microbiology 9(9): 2299-2313).*
Carleton et al. 2012 (Engineering the type III secretion system in non-replicating bacterial minicells for antigen delivery; Nature Communications 4: 1590, pp. 1-8).*
Wall et al. 2010 (Targeting Tumors with *Salmonella typhimurium*—Potential for Therapy; Oncotarget 1: 721-728) (Year: 2010).*

(Continued)

*Primary Examiner* — Mary Maille Lyons
(74) *Attorney, Agent, or Firm* — Medlen & Carroll, LLP

(57) ABSTRACT

The invention provides compositions and methods for reducing one or more symptoms of disease by administering compositions comprising SipA. The invention's compositions and methods are particularly advantageous in reducing symptoms of diseases that are associated with overexpression of P-gp and/or p53. The invention's compositions and methods are useful in reducing cancer symptom and/or cancer multidrug resistance (MDR). The invention provides a method for reducing one or more symptoms of cancer in a mammalian subject in need thereof, comprising administering to said subject a composition comprising purified SipA. In one embodiment, said SipA is operably conjugated to a nanoparticle. In another embodiment, said cancer comprises cancer cells resistant to at least one cytotoxin.

2 Claims, 11 Drawing Sheets
Specification includes a Sequence Listing.

(56) References Cited

U.S. PATENT DOCUMENTS

| | | | | |
|---|---|---|---|---|
| 7,727,554 | B2 | 6/2010 | Labhasetwar et al. | 424/489 |
| 8,063,131 | B2 | 11/2011 | Gao | 524/434 |
| 8,193,334 | B2 | 6/2012 | Radovic-Moreno et al. | 536/24.5 |
| 8,246,968 | B2 | 8/2012 | Zale et al. | 424/400 |
| 8,318,208 | B1 | 11/2012 | Zale et al. | 424/489 |
| 8,318,211 | B2 | 11/2012 | Zale et al. | 424/501 |
| 8,323,694 | B2 | 12/2012 | Hainfeld | 424/489 |
| 2004/0151724 | A1 | 8/2004 | Coronella-Wood | 424/155.1 |
| 2006/0159687 | A1 | 7/2006 | Buckley et al. | 424/155.1 |
| 2009/0226942 | A1 | 9/2009 | MacKenzie et al. | 435/7.23 |
| 2010/0247440 | A1 | 9/2010 | Morton | 424/9.2 |
| 2011/0129526 | A1 | 6/2011 | Wang et al. | 424/450 |
| 2012/0302516 | A1 | 11/2012 | Nantz et al. | 514/34 |

FOREIGN PATENT DOCUMENTS

| | | |
|---|---|---|
| EP | A 185225 | 6/1986 |
| EP | 275966 | 7/1988 |
| EP | A 275966 | 7/1988 |
| EP | A 296321 | 12/1988 |
| EP | A 434960 | 3/1991 |
| FR | 2683529 | 5/2014 |
| JP | A 52-089680 | 7/1977 |
| JP | A 53-149985 | 12/1978 |
| JP | A55-059173 | 2/1980 |
| JP | 8280396 | 5/1982 |
| JP | A 57-080396 | 5/1982 |
| JP | 84219300 | 10/1984 |
| SU | 1336489 | 2/1990 |
| WO | WO 88/06158 | 8/1988 |
| WO | WO 1999/045120 A2 | 9/1999 |
| WO | WO 2000/059537 | 10/2000 |
| WO | WO 2004/078097 | 9/2004 |
| WO | WO 2006/042146 A2 | 4/2006 |
| WO | WO 2008/091375 | 7/2008 |
| WO | WO 2008/151049 | 12/2008 |
| WO | WO 2010/046900 A2 | 4/2010 |
| WO | WO 2011/057146 | 4/2011 |
| WO | WO 2012/103038 A2 | 8/2012 |

OTHER PUBLICATIONS

Wall et al. 2007 (Identification of the *Salmonella enterica* serotype Typhimurium SipA domain responsible for inducing neutrophil recruitment across the intestinal epithelium; Cellular Microbiology 9(9): 2299-2313); (Year: 2007).*

Carleton et al. 2012 (Engineering the type III secretion system in non-replicating bacterial minicells for antigen delivery; Nature Communications 4: 1590, pp. 1-8). (Year: 2012).*

Agbor, et al., "The Erm Protein, Ezrin, Regulates Neutrophil Transmigration by Modulating the Apical Localization of Mrp2 in Response to the Sipa Effector Protein During *Salmonella typhimurium* Infection." *Cell Microbiol*, 13(12):2007-2021 (2011).

Altschul, et al., "Basic Local Alignment Search Tool." *Journal of Molecular Biology*, 215(3):403-410 (1990).

Baird and Kaye "Drug Resistance Reversal—Are We Getting Closer?". *Eur J Cancer*, 39(17):2450-2461 (2003).

Beaudry, et al., "Loss of the P53/P63 Regulated Desmosomal Protein Perp Promotes Tumorigenesis." *PLoS Genet*, 6(10):e1001168 (2010).

Borghouts, et al., "Current Strategies for the Development of Peptide-Based Anti-Cancer Therapeutics." *Journal of Peptide Science*, 11(11):713-726 (2005).

Bronstein, et al., "Invb Is a Type Iii Secretion Chaperone Specific for Sspa." *J Bacteriol*, 182(23):6638-6644 (2000).

Chan, et al., "P-Glycoprotein Expression: Critical Determinant in the Response to Osteosarcoma Chemotherapy." *JNCI: Journal of the National Cancer Institute*, 89(22):1706-1715 (1997).

Chang, et al., "A Novel Peptide Enhances Therapeutic Efficacy of Liposomal Anti-Cancer Drugs in Mice Models of Human Lung Cancer." *PLoS One*, 4(1):e4171 (2009).

Criss, et al., "Regulation of *Salmonella*-Induced Neutrophil Transmigration by Epithelial Adp-Ribosylation Factor 6." *J Biol Chem*, 276(51):48431-48439 (2001).

Davies, et al., "Perp Expression Stabilizes Active P53 Via Modulation of P53-Mdm2 Interaction in Uveal Melanoma Cells." *Cell Death and Dis*, 2:e136 (2011).

Diaz, et al., "Pharmacologic and Toxicologic Evaluation of C. Novyi-Nt Spores." *Toxicological Sciences*, 88(2):562-575 (2005).

Engert, et al., "A Phase-I Study of an Anti-Cd25 Ricin a-Chain Immunotoxin (Rft5-Smpt-Dga) in Patients with Refractory Hodgkin's Lymphoma." *Blood*, 89(2):403-410 (1997).

Faisal, et al., "Leptosome-Entrapped Leptospiral Antigens Conferred Significant Higher Levels of Protection Than Those Entrapped with Pc-Liposomes in a Hamster Model." *Vaccine*, 27(47):6537-6545 (2009).

Figueiredo, et al., "*Salmonella enterica typhimurium* Sipa Induces Cxc-Chemokine Expression through P38mapk and Jun Pathways." *Microbes Infect*, 11(2):302-310 (2009).

Fojo and Bates, "Strategies for Reversing Drug Resistance." *Oncogene*, 22(47):7512-7523 (2003).

Galkin, et al., "The Bacterial Protein Sipa Polymerizes G-Actin and Mimics Muscle Nebulin." *Nat Struct Mol Biol*, 9(7):518-521 (2002).

Ghobrial, et al., "Targeting Apoptosis Pathways in Cancer Therapy." *CA: A Cancer Journal for Clinicians*, 55(3):178-194 (2005).

Gottesman, et al., "Multidrug Resistance in Cancer: Role of Atp-Dependent Transporters." *Nat Rev Cancer*, 2(1):48-58 (2002).

Haraga, et al., "Salmonellae Interplay with Host Cells." *Nat Rev Micro*, 6(1):53-66 (2008).

Ho, et al., "Multidrug Resistance 1 Gene (P-Glycoprotein 170): An Important Determinant in Gastrointestinal Disease?". *Gut*, 52(5):759-766 (2003).

Hong, et al., "Control of Protein Structure and Function through Surface Recognition by Tailored Nanoparticle Scaffolds." *Journal of the American Chemical Society*, 126(3):739-743 (2004).

Huse, et al., "Generation of a Large Combinatorial Library of the Immunoglobulin Repertoire in Phage Lambda." *Science*, 246(4935):1275-1281 (1989).

Huwyler, et al., "Tumor Targeting Using Liposomal Antineoplastic Drugs." *International Journal of Nanomedicine*, 3(1):21-29 (2008).

Johnstone, et al., "Multiple Physiological Functions for Multidrug Transporter P-Glycoprotein?". *Trends Biochem Sci*, 25(1):1-6 (2000).

Jones, et al., "P-Glycoprotein and Transporter Mrpl Reduce HIV Protease Inhibitor Uptake in CD4 Cells: Potential for Accelerated Viral Drug Resistance?". *Aids*, 15(11):1353-1358 (2001).

Juliano and Ling "A Surface Glycoprotein Modulating Drug Permeability in Chinese Hamster Ovary Cell Mutants." *Biochimica et Biophysica Acta (BBA)—Biomembranes*, 455(1):152-162 (1976).

Karlin and Altschul "Methods for Assessing the Statistical Significance of Molecular Sequence Features by Using General Scoring Schemes." *Proceedings of the National Academy of Sciences*, 87(6):2264-2268 (1990).

Karlin and Altschul "Applications and Statistics for Multiple High-Scoring Segments in Molecular Sequences." *Proceedings of the National Academy of Sciences*, 90(12):5873-5877 (1993).

Keestra, et al., "A *Salmonella* Virulence Factor Activates the Nodl/Nod2 Signaling Pathway." *MBio*, 2(6) (2011).

Kooij, et al., "P-Glycoprotein Acts as an Immunomodulator During Neuroinflammation." *PLoS One*, 4(12):e8212 (2009).

Kubota, et al., "Reduced Hgf Expression in Subcutaneous Ct26 Tumor Genetically Modified to Secrete Nk4 and Its Possible Relation with Antitumor Effects." *Cancer Science*, 95(4):321-327 (2004).

Lee, et al., "A Secreted *Salmonella* Protein Induces a Proinflammatory Response in Epithelial Cells, Which Promotes Neutrophil Migration." *Proceedings of the National Academy of Sciences*, 97(22):12283-12288 (2000).

Leith, et al., "Frequency and Clinical Significance of the Expression of the Multidrug Resistance Proteins Mdr1/P-Glycoprotein, Mrp1, and Lrp in Acute Myeloid Leukemia: A Southwest Oncology Group Study." *Blood*, 94(3):1086-1099 (1999).

Levine, "P53, the Cellular Gatekeeper for Growth and Division." *Cell*, 88(3):323-331 (1997).

(56) References Cited

OTHER PUBLICATIONS

Mantovani, et al., "Caspase-Dependent Cleavage of 170-Kda P-Glycoprotein During Apoptosis of Human T-Lymphoblastoid Cem Cells." *Journal of Cellular Physiology*, 207(3):836-844 (2006).
Mizukami, et al., "Induction of Interleukin-8 Preserves the Angiogenic Response in Hif-1[Alpha]-Deficient Colon Cancer Cells." *Nat Med*, 11(9):992-997 (2005).
Mrsny, et al., "Identification of Hepoxilin A3 in Inflammatory Events: A Required Role in Neutrophil Migration across Intestinal Epithelia." *Proc Natl Acad Sci U S A*, 101(19):7421-7426 (2004).
Pawelek, et al., "Tumor-Targeted <Em>Salmonella</Em> as a Novel Anticancer Vector." *Cancer Research*, 57(20):4537-4544 (1997).
Pazos, et al., "Multidrug Resistance-Associated Transporter 2 Regulates Mucosal Inflammation by Facilitating the Synthesis of Hepoxilin a<Sub>3</Sub>." *The Journal of Immunology*, 181(11):8044-8052 (2008).
Rana, et al., "Monolayer Coated Gold Nanoparticles for Delivery Applications." *Advanced Drug Delivery Reviews*, 64(2):200-216 (2012).
Ren, et al., "Macrophage Migration Inhibitory Factor Stimulates Angiogenic Factor Expression and Correlates with Differentiation and Lymph Node Status in Patients with Esophageal Squamous Cell Carcinoma." *Ann Surg*, 242(1):55-63 (2005).
Sadanand, et al., "Effect of Psc 833, a Potent Inhibitor of P-Glycoprotein, on the Growth of Astrocytoma Cells in Vitro." *Cancer Letters*, 198(1):21-27 (2003).
Schlumberger, et al., "Two Newly Identified Sipa Domains (F1, F2) Steer Effector Protein Localization and Contribute to *Salmonella* Host Cell Manipulation." *Mol Microbiol*, 65(3):741-760 (2007).
Siccardi, et al., "<Em>Salmonella enterica</Em> Serovar *typhimurium* Modulates P-Glycoprotein in the Intestinal Epithelium." *American Journal of Physiology—Gastrointestinal and Liver Physiology*, 294(6):G1392-G1400 (2008).
Silva, et al., "*Salmonella typhimurium* Sipa-Induced Neutrophil Transepithelial Migration: Involvement of a Pkc-Alpha-Dependent Signal Transduction Pathway." *Am J Physiol Gastrointest Liver Physiol*, 286(6):G1024-1031 (2004).
Song, et al., "Peptide Ligand-Mediated Liposome Distribution and Targeting to Egfr Expressing Tumor in Vivo." *International Journal of Pharmaceutics*, 363(1):155-161 (2008).
Soussi and Beroud "Assessing Tp53 Status in Human Tumours to Evaluate Clinical Outcome." *Nat Rev Cancer*, 1(3):233-240 (2001).
Srikanth, et al., "<Em>Salmonella</Em> Pathogenesis and Processing of Secreted Effectors by Caspase-3." *Science*, 330(6002):390-393 (2010).
Tada, et al., "Increased Expression of Multidrug Resistance-Associated Proteins in Bladder Cancer During Clinical Course and Drug Resistance to Doxorubicin." *International Journal of Cancer*, 98(4):630-635 (2002).
Tien, et al., "In Vitro and in Vivo Characterization of a Potential Universal Placebo Designed for Use in Vaginal Microbicide Clinical Trials." *AIDS Res Hum Retroviruses*, 21(10):845-853 (2005).

Trock, et al., "Multidrug Resistance in Breast Cancer: A Meta-Analysis of Mdr1/Gp170 Expression and Its Possible Functional Significance." *JCNI: Journal of the National Cancer Institute*, 89(13):917-931 (1997).
Vallbohmer, et al., "Molecular Determinants of Cetuximab Efficacy." *J Clin Oncol*, 23(15):3536-3544 (2005).
van de Ven, et al., "Abc Drug Transporters and Immunity: Novel Therapeutic Targets in Autoimmunity and Cancer." *J Leukoc Biol*, 86(5):1075-1087 (2009).
Vogelstein, et al., "Surfing the P53 Network." *Nature*, 408(6810):307-310 (2000).
Voinea and Simionescu "Designing of 'Intelligent' Liposomes for Efficient Delivery of Drugs." *Journal of Cellular and Molecular Medicine*, 6(4):465-474 (2002).
Wall, et al., "Identification of the *Salmonella enterica* Serotype *typhimurium* Sipa Domain Responsible for Inducing Neutrophil Recruitment across the Intestinal Epithelium." *Cellular Microbiology*, 9(9):2299-2313 (2007).
Wang, et al., "Antitumor Activity and Immune Response Induction of a Dual Agonist of Toll-Like Receptors 7 and 8." *Molecular Cancer Therapeutics*, 9(6):1788-1797 (2010a).
Wang and Thanou "Targeting Nanoparticles to Cancer." *Pharmacol Res*, 62(2):90-99 (2010b).
Wiemann and Starnes "Coley's Toxins, Tumor Necrosis Factor and Cancer Research: A Historical Perspective." *Pharmacology & Therapeutics*, 64(3):529-564 (1994).
Yagi, et al., "Expression of Multidrug Resistance 1 Gene in B-Cell Lymphomas: Association with Follicular Dendritic Cells." *Histopathology*, 62(3):414-420 (2013).
Yu, et al., "April and Tall-I and Receptors Bcma and Taci: System for Regulating Humoral Immunity." *Nat Immunol*, 1(3):252-256 (2000).
Zhou, et al., "Role of the *S. typhimurium* Actin-Binding Protein Sipa in Bacterial Internalization." *Science*, 283(5410):2092-2095 (1999).
Zitzmann, et al., "Arginine-Glycine-Aspartic Acid (Rgd)-Peptide Binds to Both Tumor and Tumor-Endothelial Cells in Vivo." *Cancer Res*, 62(18):5139-5143 (2002).
Anuchapreeda, et al., "Modulation of P-Glycoprotein Expression and Function by Curcumin in Multidrug-Resistant Human Kb Cells." *Biochem Pharmacol*, 64(4):573-582 (2002).
Carleton, et al., "Engineering the Type III Secretion System in Non-Replicating Bacterial Minicells for Antigen Delivery." 4:1590 (2013).
Dunn, et al., "Overexpression of a P-Glycoprotein in Hepatocellular Carcinomas from Woodchuck Hepatitis Virus-Infected Woodchucks (*Marmota monax*)." *Hepatology*, 23(4):662-668 (1996).
Sharma, et al., "Nanocarriers for Diagnosis and Targeting of Breast Cancer." *BioMed Research International*, 2013:10 (2013).
Mesa-Pereira, et al., "Novel Tools to Analyze the Function of *Salmonella* Effectors Show That Svpb Ectopic Expression Induces Cell Cycle Arrest in Tumor Cells." *PLoS One*, 8(10):e78458 (2013).
Toley and Forbes "Motility Is Critical for Effective Distribution and Accumulation of Bacteria in Tumor Tissue." *Integrative Biology*, 4(2):165-176 (2012).

* cited by examiner

SipA exemplary amino acid sequence SEQ ID NO:01 of Salmonella enterica subsp. enterica serovar Typhimurium str. SL1344 (GenBank: AAA86618.1)

```
  1 mvtsvrtqpp vimpgmqtei ktqatnlaan lsavrakchs davreikgpq ledfpalikq
 61 asldalfkcg kdaealkevf tnsnnvagkk aimefaglfr salnatsdsp eaktllmkvg
121 aeyaaqilkd glkeksafgp wlpetkkaea klenlokqll diiknntgge lsklstnlvm
181 qevrpyiasc iehnfgctld pltrsnlthl vdkaaakave aldmcpqklt qeqgtsvgre
241 arhlemqtli plllrnvfaq ipadklpdpk ipepaagpvp dggkkaeptg inininidss
301 nhsvdnskhi nnaepvdngq rhidnsnhdn srktidnsrt fidnsqrnge shhstnssnv
361 shshsrvdst thqtetahsa stgaidhgia gkidvtahat aeavtnasse skdgkvvtse
421 kgttgettsf dovdgvtsks ligkpvqatv hgvddnkqqs qtaeivnvkp lasqlagven
481 vktdtlqsdt tvitgnkaqt tdndnsqtdk tgpfsglkfk qnsflstvps vtnmhsmhfd
541 aretflqvir kalepdtstp fpvrrafdgl raeilpndti ksaalkaqcs didkhpelka
601 kmetlkevit hhpqkeklae ialqfareag ltrlkgetdy vlsnvldgli gdgswragpa
661 yesylnkpgv drvittvdgl hmqr
```

Figure 7

FIG. 10A — Homo sapiens PERP amino acid sequence (SEQ ID NO:02) (NCBI Reference Sequence: NM_022121.4)

MIRCGLACERCRWILPLLLLSAIAFDIIALAGRGWLQSSDHGQT

SSLWWKCSQEGGGSGSYEEGCQSLMEYAWGRAAAAMLFCGFIILVICFILSFFALCGP

QMLVFLRVIGGLLALAAVFQIISLVIYPVKYTQTFTLHANPAVTYIYNWAYGFGWAAT

IILIGCAFFFCCLPNYEDDLLGNAKPRYFYTSA

FIG. 10B — Homo sapiens PERP nucleotide sequence (SEQ ID NO:03) (NCBI Reference Sequence: NM_022121.4)

```
   1 ctctgagtca ccggaatcta ggtggggccg cccggagcgg cgtcctcggg agccgcctcc
  61 ccgcggcctc ttcgcttttg tggcggcgcc cgcgctcgca ggccactctc tgctgtcgcc
 121 cgtcccgcgc gctcctccga cccgctccgc tccgctccgc tcggccccgc gccgcccgtc
 181 aacatgatcc gctgcggcct ggctgcgag cgctgccgct ggatcctgcc cctgctccta
 241 ctcagcgcca tcgccttcga catcatcgcg ctggccggcc gcggctggtt gcagtctagc
 301 gaccacggcc agacgtcctc gctgtggtgg aaatgctccc aagagggcgg cggcagcggg
 361 tcctacgagg agggctgtca gagcctcatg gagtacgcgt ggggtagagc agcggctgcc
 421 atgctcttct gtggcttcat catcctggtg atctgtttca tcctctcctt cttcgccctc
 481 tgtggacccc agatgcttgt cttcctgaga gtgattggag gtctccttgc cttggctgct
 541 gtgttccaga tcatctccct ggtaatttac cccgtgaagt acacccagac cttcacccttg
 601 catgccaacc ctgctgtcac ttacatctat aactgggcct acggctttgg gtgggcagcc
 661 acgattatcc tgattggctg tgccttcttc ttctgctgcc tccccaacta cgaagatgac
 721 cttctgggca atgccaagcc caggtacttc tacacatctg cctaacttgg gaatgaatgt
 781 gggagaaaat cgctgctgct gagatggact ccagaagaag aaactgtttc tccaggcgac
 841 tttgaaccca ttttttggca gtgttcatat tattaaacta gtcaaaaatg ctaaaataat
 901 ttgggagaaa atatttttta agtagtgtta tagtttcatg tttatctttt attatgtttt
 961 gtgaagttgt gtcttttcac taattaccta tactatgcca atatttcctt atatctatcc
1021 ataacattta tactacattt gtaagagaat atgcacgtga aacttaacac tttataaggt
1081 aaaaatgagg tttccaagat ttaataatct gatcaagttc ttgttatttc caaatagaat
1141 ggactcggtc tgttaagggc taaggagaag aggaagataa ggttaaaagt tgttaatgac
1201 caaacattct aaaagaaatg caaaaaaaaa gtttattttc aagccttcga actatttaag
1261 gaaagcaaaa tcatttccta aatgcatatc atttgtgaga atttctcatt aatatcctga
1321 atcattcatt ttagctaagg cttcatgttg actcgatatg tcatctagga aagtactatt
1381 tcatggtcca aacctgttgc catagttggt aaggctttcc tttaagtgtg aaatatttag
1441 atgaaatttt ctcttttaaa gttctttata gggttagggt gtgggaaaat gctatattaa
1501 taaatctgta gtgttttgtg tttatatgtt cagaaccaga gtagactgga ttgaaagatg
1561 gactgggtct aatttatcat gactgataga tctggttaag ttgtgtagta aagcattagg
1621 agggtcattc ttgtcacaaa agtgccacta aaacagcctc aggagaataa atgacttgct
1681 tttctaaatc tcaggtttat ctgggctcta tcatatagac aggcttctga tagtttgcaa
1741 ctgtaagcag aaacctacat atagttaaaa tcctggtctt tcttggtaaa cagatttaa
1801 atgtctgata taaacatgc cacaggagaa ttcggggatt tgagtttctc tgaatagcat
1861 atatatgatg catcggatag gtcattatga ttttttacca tttcgactta cataatgaaa
1921 accaattcat tttaaatatc agattattat tttgtaagtt gtggaaaaag ctaattgtag
1981 ttttcattat gaagttttcc caataaacca ggtattctaa acttgtttcc agtttgtagt
```

FIGURE 10A and 10B

```
2041 ttttccattt ttcaaatctg gggaaaggaa ttaaaaaaaa aatgggtaat aagaacatgg
2101 gatataatga aaagtggttt ttgtttgttt ttttgtttga agttttaagg gccttgctca
2161 ttttaggtgt ccaaaaccaa tttttgagtg gagattaatg aattctaata gtctattccc
2221 tgaacttttc ctcaatgaac aatacccctag acacacatta aacaatttct ctgcagtgct
2281 atcaaccaga ggaaaatgga ctaagagatt tctggcaggt tcagacaccc gggggacatg
2341 tgtgcagtgt agctgaagcc tcctccttgt gctggggtcc ccttccattc aggtggtggg
2401 gtagcagtct ctctatttc cccttgccct ccttcccatt ttatcatttg ttatttttt
2461 tcccaccata agtcatatgt tacttccact atggtgtatg tcattgtgag gatgggtgca
2521 gagaggctgg gtgggagaac ggaaatatat ctccctaggg ctactgttgg ccagctagtc
2581 cttggcagtg aattttcta tgcttttcaa aatgcgaggt gaatgtttct catagagaaa
2641 tgtaatctgg gtgattatac caaaattgaa aagaaaaacc cacacaacta tgccgtggct
2701 ggtggagaat ttgaagtggt cattaaaaat gttaaaaatc ccatctttta aagtgatacc
2761 acagctcatt caagaagata ctggatatct agagattaag aaacgtggtc tcctgttaaa
2821 catgaaaatg actccgttta taagcttctc taccacatgc acttgtcttt gcatgatttc
2881 ccatccagcc ttcttcccct cctcaatcac acaataccct aacggcgcac atttaggaaa
2941 aatgcaacct cctgggacca acgagcctga tataatagaa ccatgtcaac ctaaagtatt
3001 tatgacaaag ataaactctt attttgcaga aatggtctgc ttccttcagc cttgttctag
3061 tatagagatc tgccattcct tgttgatcca gattcaccaa gacagatacc tttatgtcat
3121 aacagaaggg aagttccaga ggattctgga gagtaatgaa gaattgggct gagaaaccac
3181 ctgaaggcta acagtgcatt gcatgagatt tcccacagta aagctgaggt gcttttggt
3241 tcagtaatta aatattgagt tcccacccctt taaataagca gttctaggtt cctaagcaat
3301 tatttcactc tgtaagtagc cagacatgct aagtggcact tactgctgat tgtaacaaag
3361 aagtaatata tcaaggtctt tccatgttca cacaaggtag cttgtgtgta ataacttagc
3421 ttcaaaacca tagactgcag aactcacaag ttcaacagcc tttcctttt taaggaaatg
3481 aaaacaatgg aaaatatagt catcataact taattcggtt tattttttt ttctgtaaac
3541 tcccccctgaa agacattcct attaatacag taaatgtgaa cactgacttg tttttataag
3601 cacatctgaa agggcatatt tgagtctcat cccaactttg gtccttgcta tctgtgcagg
3661 cttgggcagg tcatctccct gctggtctca atatcctcac ctgtaaaatg attgtaaatg
3721 atcccctac cttcaagatt ctctgattga tagaattttt tctttaatta aaaaatttta
3781 aatattcctt gagttggaag cactgatcaa taagtggatt gcttagggag gttggaacga
3841 atagattcag tcccaacttc ctcttttaaa ttccctcttc ctcactcttc ctgcaacact
3901 tattttaca gttgagtttt aaaaataagt aatatataaa ataatttctg tagtgtggtt
3961 tcagatttaa aaattcctgc agacaggctg ggcttgcaac cccatcagtc gatggtcaga
4021 gcccttgct ttttgagacc atttttaggt gagcttggct tgcctggata cagtgtgcag
4081 tgcattcttc ctgaattttg caattctggt atctgggtgt attttctagg tgtgtcaggg
4141 tgagtgtaat ccacctaggg tgtggaaaaa gccaagaaag ggaaattaaa agaggttcct
4201 atccagtcat gttaatgatc ttccacttgt actatcctgt gcttcgttgt taacctcgaa
4261 aacatacttt gttggctgca aaataaaca aagggaaact caaaaaaaaa aaaaaaaaa
```

FIGURE 10B Continued

SEQUENCE LISTING

```
<160> NUMBER OF SEQ ID NOS: 3

<210> SEQ ID NO 1
<211> LENGTH: 684
<212> TYPE: PRT
<213> ORGANISM: Salmonella enterica subsp. enterica serovar Typhimurium
      str. SL1344

<400> SEQUENCE: 1

Met Val Thr Ser Val Arg Thr Gln Pro Pro Val Ile Met Pro Gly Met
1               5                   10                  15

Gln Thr Glu Ile Lys Thr Gln Ala Thr Asn Leu Ala Ala Asn Leu Ser
            20                  25                  30

Ala Val Arg Ala Lys Cys His Ser Asp Ala Val Arg Glu Ile Lys Gly
        35                  40                  45

Pro Gln Leu Glu Asp Phe Pro Ala Leu Ile Lys Gln Ala Ser Leu Asp
    50                  55                  60

Ala Leu Phe Lys Cys Gly Lys Asp Ala Glu Ala Leu Lys Glu Val Phe
65                  70                  75                  80

Thr Asn Ser Asn Asn Val Ala Gly Lys Lys Ala Ile Met Glu Phe Ala
                85                  90                  95

Gly Leu Phe Arg Ser Ala Leu Asn Ala Thr Ser Asp Ser Pro Glu Ala
            100                 105                 110

Lys Thr Leu Leu Met Lys Val Gly Ala Glu Tyr Ala Ala Gln Ile Ile
        115                 120                 125

Lys Asp Gly Leu Lys Glu Lys Ser Ala Phe Gly Pro Trp Leu Pro Glu
    130                 135                 140

Thr Lys Lys Ala Glu Ala Lys Leu Glu Asn Leu Glu Lys Gln Leu Leu
145                 150                 155                 160

Asp Ile Ile Lys Asn Asn Thr Gly Gly Glu Leu Ser Lys Leu Ser Thr
                165                 170                 175

Asn Leu Val Met Gln Glu Val Met Pro Tyr Ile Ala Ser Cys Ile Glu
            180                 185                 190

His Asn Phe Gly Cys Thr Leu Asp Pro Leu Thr Arg Ser Asn Leu Thr
        195                 200                 205
```

His Leu Val Asp Lys Ala Ala Ala Lys Ala Val Glu Ala Leu Asp Met
    210                 215                 220

Cys Pro Gln Lys Leu Thr Gln Glu Gln Gly Thr Ser Val Gly Arg Glu
225                 230                 235                 240

Ala Arg His Leu Glu Met Gln Thr Leu Ile Pro Leu Leu Leu Arg Asn
                245                 250                 255

Val Phe Ala Gln Ile Pro Ala Asp Lys Leu Pro Asp Pro Lys Ile Pro
                260                 265                 270

Glu Pro Ala Ala Gly Pro Val Pro Asp Gly Gly Lys Lys Ala Glu Pro
            275                 280                 285

Thr Gly Ile Asn Ile Asn Ile Asn Ile Asp Ser Ser Asn His Ser Val
        290                 295                 300

Asp Asn Ser Lys His Ile Asn Asn Ala Glu Pro Val Asp Asn Gly Gln
305                 310                 315                 320

Arg His Ile Asp Asn Ser Asn His Asp Asn Ser Arg Lys Thr Ile Asp
                325                 330                 335

Asn Ser Arg Thr Phe Ile Asp Asn Ser Gln Arg Asn Gly Glu Ser His
                340                 345                 350

His Ser Thr Asn Ser Ser Asn Val Ser His Ser His Ser Arg Val Asp
            355                 360                 365

Ser Thr Thr His Gln Thr Glu Thr Ala His Ser Ala Ser Thr Gly Ala
    370                 375                 380

Ile Asp His Gly Ile Ala Gly Lys Ile Asp Val Thr Ala His Ala Thr
385                 390                 395                 400

Ala Glu Ala Val Thr Asn Ala Ser Ser Glu Ser Lys Asp Gly Lys Val
                405                 410                 415

Val Thr Ser Glu Lys Gly Thr Thr Gly Glu Thr Thr Ser Phe Asp Glu
                420                 425                 430

Val Asp Gly Val Thr Ser Lys Ser Ile Ile Gly Lys Pro Val Gln Ala
            435                 440                 445

Thr Val His Gly Val Asp Asp Asn Lys Gln Gln Ser Gln Thr Ala Glu
    450                 455                 460

Ile Val Asn Val Lys Pro Leu Ala Ser Gln Leu Ala Gly Val Glu Asn
465                 470                 475                 480

Val Lys Thr Asp Thr Leu Gln Ser Asp Thr Thr Val Ile Thr Gly Asn
                485                 490                 495

Lys Ala Gly Thr Thr Asp Asn Asp Asn Ser Gln Thr Asp Lys Thr Gly
            500                 505                 510

Pro Phe Ser Gly Leu Lys Phe Lys Gln Asn Ser Phe Leu Ser Thr Val
        515                 520                 525

Pro Ser Val Thr Asn Met His Ser Met His Phe Asp Ala Arg Glu Thr
530                 535                 540

Phe Leu Gly Val Ile Arg Lys Ala Leu Glu Pro Asp Thr Ser Thr Pro
545                 550                 555                 560

Phe Pro Val Arg Arg Ala Phe Asp Gly Leu Arg Ala Glu Ile Leu Pro
                565                 570                 575

Asn Asp Thr Ile Lys Ser Ala Ala Leu Lys Ala Gln Cys Ser Asp Ile
                580                 585                 590

Asp Lys His Pro Glu Leu Lys Ala Lys Met Glu Thr Leu Lys Glu Val
            595                 600                 605

Ile Thr His His Pro Gln Lys Glu Lys Leu Ala Glu Ile Ala Leu Gln
    610                 615                 620

Phe Ala Arg Glu Ala Gly Leu Thr Arg Leu Lys Gly Glu Thr Asp Tyr

```
              625                 630                 635                 640
Val Leu Ser Asn Val Leu Asp Gly Leu Ile Gly Asp Gly Ser Trp Arg
                      645                 650                 655

Ala Gly Pro Ala Tyr Glu Ser Tyr Leu Asn Lys Pro Gly Val Asp Arg
              660                 665                 670

Val Ile Thr Thr Val Asp Gly Leu His Met Gln Arg
              675                 680
```

<210> SEQ ID NO 2
<211> LENGTH: 193
<212> TYPE: PRT
<213> ORGANISM: Homo sapiens

<400> SEQUENCE: 2

```
Met Ile Arg Cys Gly Leu Ala Cys Glu Arg Cys Arg Trp Ile Leu Pro
 1               5                  10                  15

Leu Leu Leu Leu Ser Ala Ile Ala Phe Asp Ile Ile Ala Leu Ala Gly
                20                  25                  30

Arg Gly Trp Leu Gln Ser Ser Asp His Gly Gln Thr Ser Ser Leu Trp
            35                  40                  45

Trp Lys Cys Ser Gln Glu Gly Gly Ser Gly Ser Tyr Glu Glu Cys Gly
    50                  55                  60

Cys Gln Ser Leu Met Glu Tyr Ala Trp Gly Arg Ala Ala Ala Ala Met
65                  70                  75                  80

Leu Phe Cys Gly Phe Ile Ile Leu Val Ile Cys Phe Ile Leu Ser Phe
                85                  90                  95

Phe Ala Leu Cys Gly Pro Gln Met Leu Val Phe Leu Arg Val Ile Gly
            100                 105                 110

Gly Leu Leu Ala Leu Ala Ala Val Phe Gln Ile Ile Ser Leu Val Ile
        115                 120                 125

Tyr Pro Val Lys Tyr Thr Gln Thr Phe Thr Leu His Ala Asn Pro Ala
130                 135                 140

Val Thr Tyr Ile Tyr Asn Trp Ala Tyr Gly Phe Gly Trp Ala Ala Thr
145                 150                 155                 160

Ile Ile Leu Ile Gly Cys Ala Phe Phe Cys Cys Leu Pro Asn Tyr
                165                 170                 175

Glu Asp Asp Leu Leu Gly Asn Ala Lys Pro Arg Tyr Phe Tyr Thr Ser
            180                 185                 190

Ala
```

<210> SEQ ID NO 3
<211> LENGTH: 4319
<212> TYPE: DNA
<213> ORGANISM: Homo sapiens

<400> SEQUENCE: 3

```
ctctgagtca ccggaatcta ggtggggccg cccggagcgg cgtcctcggg agccgcctcc      60
ccgcggcctc ttcgcttttg tggcggcgcc cgcgctcgca ggccactctc tgctgtcgcc     120
cgtcccgcgc gctcctccga cccgctccgc tccgctccgc tcggccccgc gccgcccgtc     180
aacatgatcc gctgcggcct ggcctgcgag cgctgccgct ggatcctgcc cctgctccta     240
ctcagcgcca tcgccttcga catcatcgcg ctggcggcc gcggctggtt gcagtctagc     300
gaccacggcc agacgtcctc gctgtggtgg aaatgctccc aagagggcgg cggcagcggg     360
tcctacgagg agggctgtca gagcctcatg gagtacgcgt ggggtagagc agcggctgcc     420
```

```
atgctcttct gtggcttcat catcctggtg atctgtttca tcctctcctt cttcgccctc    480
tgtggacccc agatgcttgt cttcctgaga gtgattggag gtctccttgc cttggctgct    540
gtgttccaga tcatctccct ggtaatttac cccgtgaagt acacccagac cttcacccttt   600 catgccaacc ctgctgtcac ttacatctat aactgggcct acggctttgg gtgggcagcc    660
acgattatcc tgattggctg tgccttcttc ttctgctgcc tccccaacta cgaagatgac    720
cttctgggca tgccaagcc caggtacttc tacacatctg cctaacttgg gaatgaatgt     780
gggagaaaat cgctgctgct gagatggact ccagaagaag aaactgtttc tccaggcgac    840
tttgaaccca ttttttggca gtgttcatat tattaaacta gtcaaaaatg ctaaaataat    900
ttgggagaaa atatttttta agtagtgtta tagtttcatg tttatctttt attatgtttt    960
gtgaagttgt gtcttttcac taattaccta tactatgcca atatttcctt atatctatcc   1020
ataacattta tactacattt gtaagagaat atgcacgtga aacttaacac tttataaggt   1080
aaaaatgagg tttccaagat ttaataatct gatcaagttc ttgttatttc caaatagaat   1140
ggactcggtc tgttaagggc taaggagaag aggaagataa ggttaaaagt tgttaatgac   1200
caaacattct aaaagaaatg caaaaaaaaa gtttattttc aagccttcga actatttaag   1260
gaaagcaaaa tcatttccta aatgcatatc atttgtgaga atttctcatt aatatcctga   1320
atcattcatt ttagctaagg cttcatgttg actcgatatg tcatctagga aagtactatt   1380
tcatggtcca aacctgttgc catagttggt aaggctttcc tttaagtgtg aaatatttag   1440
atgaaatttt ctcttttaaa gttctttata gggttagggt gtgggaaaat gctatattaa   1500
taaatctgta gtgttttgtg tttatatgtt cagaaccaga gtagactgga ttgaaagatg   1560
gactgggtct aatttatcat gactgataga tctggttaag ttgtgtagta aagcattagg   1620
agggtcattc ttgtcacaaa agtgccacta aaacagcctc aggagaataa atgacttgct   1680
tttctaaatc tcaggtttat ctgggctcta tcatatagac aggcttctga tagtttgcaa   1740
ctgtaagcag aaacctacat atagttaaaa tcctggtctt tcttggtaaa cagattttaa   1800
atgtctgata taaaacatgc cacaggagaa ttcgggatt tgagtttctc tgaatagcat    1860
atatatgatg catcggatag gtcattatga ttttttacca tttcgactta cataatgaaa   1920
accaattcat tttaaatatc agattattat tttgtaagtt gtggaaaaag ctaattgtag   1980
ttttcattat gaagttttcc caataaacca ggtattctaa acttgtttcc agtttgtagt   2040 ttttccatttt ttcaaatctg gggaaaggaa ttaaaaaaaa atgggtaat aagaacatgg    2100 gatataatga aaagtggttt ttgtttgttt ttttgtttga agttttaagg gccttgctca   2160
ttttaggtgt ccaaaaccaa ttttttgagtg gagattaatg aattctaata gtctattccc   2220
tgaacttttc ctcaatgaac aataccctag acacacatta aacaatttct ctgcagtgct   2280
atcaaccaga ggaaaatgga ctaagagatt tctggcaggt tcagacaccc ggggacatg    2340 tgtgcagtgt agctgaagcc tcctccttgt gctggggtcc ccttccattc aggtggtggg   2400
gtagcagtct ctctatttc cccttgccct ccttcccatt ttatcatttg ttattttttt    2460
tcccaccata agtcatatgt tacttccact atggtgtatg tcattgtgag gatgggtgca   2520
gagaggctgg gtgggagaac ggaaatatat ctccctaggg ctactgttgg ccagctagtc   2580
cttggcagtg aattttttcta tgcttttcaa aatgcgaggt gaatgtttct catagagaaa   2640
tgtaatctgg gtgattatac caaaattgaa aagaaaaacc cacacaacta tgccgtggct   2700
ggtggagaat ttgaagtggt cattaaaaat gttaaaaatc ccatctttta aagtgatacc   2760
acagctcatt caagaagata ctggatatct agagattaag aaacgtggtc tcctgttaaa   2820
```

```
catgaaaatg actccgttta taagcttctc taccacatgc acttgtcttt gcatgatttc      2880
ccatccagcc ttcttcccct cctcaatcac acaataccct aacggcgcac atttaggaaa      2940
aatgcaacct cctgggacca acgagcctga tataatagaa ccatgtcaac ctaaagtatt      3000
tatgacaaag ataaactctt attttgcaga aatggtctgc ttccttcagc cttgttctag      3060
tatagagatc tgccattcct tgttgatcca gattcaccaa gacagatacc tttatgtcat      3120
aacagaaggg aagttccaga ggattctgga gagtaatgaa gaattgggct gagaaaccac      3180
ctgaaggcta acagtgcatt gcatgagatt tcccacagta aagctgaggt gcttttggt       3240 tcagtaatta aatattgagt tcccaccctt taaataagca gttctaggtt cctaagcaat      3300
tatttcactc tgtaagtagc cagacatgct aagtggcact tactgctgat tgtaacaaag      3360
aagtaatata tcaaggtctt tccatgttca cacaaggtag cttgtgtgta ataacttagc      3420
ttcaaaacca tagactgcag aactcacaag ttcaacagcc tttccttttt taaggaaatg      3480
aaaacaatgg aaaatatagt catcataact taattcggtt tatttttttt ttctgtaaac      3540
tccccctgaa agacattcct attaatacag taaatgtgaa cactgacttg ttttttataag     3600 cacatctgaa agggcatatt tgagtctcat cccaactttg gtccttgcta tctgtgcagg      3660
cttgggcagg tcatctccct gctggtctca atatcctcac ctgtaaaatg attgtaaatg     3720 atcccctac cttcaagatt ctctgattga tagaattttt tctttaatta aaaaatttta      3780
aatattcctt gagttggaag cactgatcaa taagtggatt gcttagggag gttggaacga     3840
atagattcag tcccaacttc ctcttttaaa ttccctcttc ctcactcttc ctgcaacact     3900
tatttttaca gttgagtttt aaaaataagt aatatataaa ataatttctg tagtgtggtt    3960
tcagatttaa aaattcctgc agacaggctg ggcttgcaac cccatcagtc gatggtcaga     4020 gcccctttgct ttttgagacc attttaggt gagcttggct tgcctggata cagtgtgcag     4080
tgcattcttc ctgaattttg caattctggt atctgggtgt attttctagg tgtgtcaggg     4140
tgagtgtaat ccacctaggg tgtggaaaaa gccaagaaag ggaaattaaa agaggttcct     4200
atccagtcat gttaatgatc ttccacttgt actatcctgt gcttcgttgt taacctcgaa     4260
aacatacttt gttggctgca aaaataaaca aagggaaact caaaaaaaaa aaaaaaaaa     4319
```

COMPOSITIONS AND METHODS FOR TREATING DISEASE USING *SALMONELLA* T3SS EFFECTOR PROTEIN (SIPA)

This application is the U.S. National stage filing under 35 U.S.C § 371 of, and claims priority to, International Application No. PCT/US14/69707, filed on Dec. 11, 2014, now abandoned, which claims priority under 35 U.S.C. § 119(e) to U.S. Provisional Application Ser. No. 61/914,600, filed on Dec. 11, 2013, each of which is herein incorporated by reference in its entirety.

GOVERNMENT INTEREST

This invention was made with government support under Grant number DK056754 awarded by the National Institutes of Health. The Government has certain rights in the invention.

FIELD OF THE INVENTION

The invention provides compositions and methods for reducing one or more symptoms of disease by administering compositions comprising SipA. The invention's compositions and methods are particularly advantageous in reducing symptoms of diseases that are associated with overexpression of P-gp and/or p53. The invention's compositions and methods are useful in reducing cancer symptoms and/or cancer multidrug resistance (MDR).

BACKGROUND OF THE INVENTION

Current therapies used to treat disease (e.g., cancer, infection with microorganisms, etc.) have considerable limitations. For example, current chemotherapeutics used to treat many cancer patients suffer from high toxicity, poor tumor targeting, and multidrug resistance (MDR), which together often result in incomplete destruction of the tumors. These drawbacks prevent effective treatment and are associated with increased morbidity and mortality.

The ability of cancer cells to develop resistance to multiple structurally and functionally non-related cytotoxic drugs, such as multi-drug resistance, is a major barrier to effective chemotherapy and is a critical unmet need. Over the past two decades, numerous researchers across many disciplines have investigated multidrug resistance with the ultimate goal of developing novel P-gp modulators as a way to revert MDR in human cancers. Excitement in this field of drug development is bolstered by several reports documenting many agents, which modulate the function of P-gp are able to restore the cytotoxicity of chemotherapeutic drugs to MDR cells in vitro as well as in experimental tumors in vivo (6). Clinical trials with MDR modulators have also shown some response in tumors that were otherwise non-responsive to chemotherapy (7).

While constitutive P-gp expression in normal healthy tissues is believed to be an important protective mechanism against potentially toxic xenobiotics, during disease states, such as cancer, P-gp is recognized as a major barrier to the bioavailability of administered drugs and thus, resistance to chemotherapy remains an obstacle to the successful treatment of certain cancers (Johnstone et al. (2000), Ho et al. (2003)). Recent chemotherapeutic strategies have integrated the use of hammerhead ribozymes against the MDR1 gene (encodes for P-gp) and MDR1 targeted anti-sense oligonucleotides (Fojo et al., 2003). Yet, despite these advances, all MDR inhibitors in development that have progressed to the stage of clinical trials have been generally ineffective or only effective at highly toxic doses (Baird et al., 2003). In addition, many of these modulators adversely influence the pharmacokinetics and bio-distribution of co-administered chemotherapeutic drugs. Moreover, although siRNA mediated silencing of P-gp is a promising approach, this method may genetically alter cell fate and require delicate constructed delivery systems that has, thus far, hampered its clinic usage.

Despite advances in the field, all MDR inhibitors in development that have progressed to the stage of clinical trials have been widely ineffective or only effective at highly toxic doses (8). Furthermore, since most of the prior art modulators adversely influence the pharmacokinetics and biodistribution of co-administered chemotherapeutic drugs, there remains a need for new, effective MDR and/or P-gp modulators without the undesired side effects (4).

BRIEF DESCRIPTION OF THE DRAWINGS

FIG. 7: SipA exemplary amino acid sequence SEQ ID NO:01 of *Salmonella enterica* subsp. *enterica* serovar *Typhimurium* str. SL1344 (GenBank: AAA86618.1) encoded by the DNA sequence (Locus taq) SL1344_2861 of the *Salmonella enterica* subsp. *enterica* serovar *Typhimurium* str. SL1344, complete genome sequence (NCBI Reference Sequence: NC_016810.1).

FIG. 10: Exemplary homo sapiens PERP amino acid sequence SEQ ID NO:02 (A) encoded by nucleotide sequence SEQ ID NO:03 (B) (NCBI Reference Sequence: NM_022121.4).

DEFINITIONS

Figure 1:
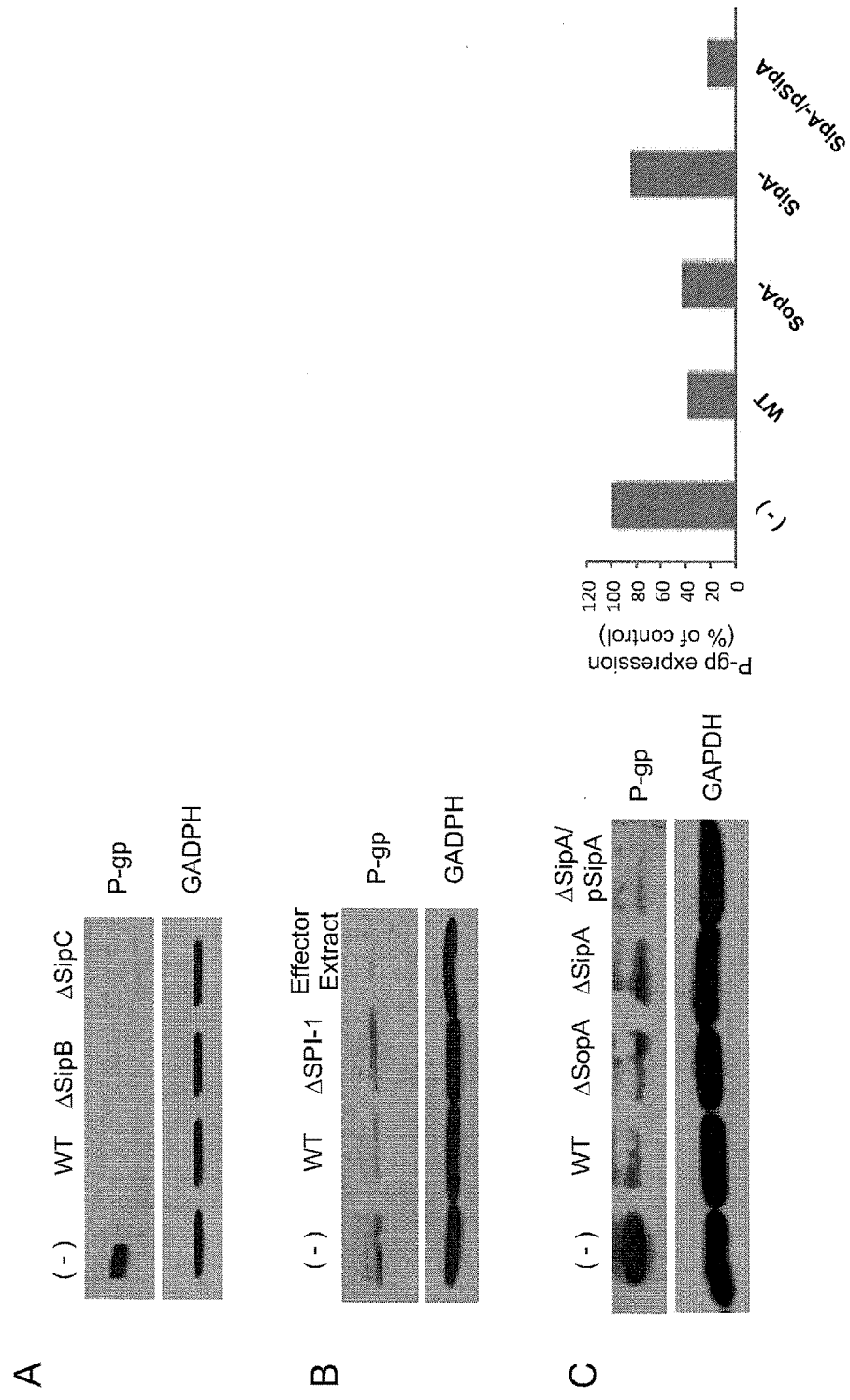
FIG. 1. The *S. Typhimurium* effector protein SipA modulates the expression of P-gp by an extracellular effect. (A) HCT8 intestinal epithelial cell monolayers were left untreated (-) or infected with wild type (WT) *S. Typhimurium* SL1344 or SL1344 type III secretion system translocon mutant strains (ΔsipB or ΔsipC) for 5 h. Whole cell lysates were normalized for protein levels and probed for P-gp. GAPDH probing served as a loading control. (B) HCT8 cells were infected with wild type SL1344 or an SL1344 SPI-1 deficient mutant strain, or exposed to wild-type SL1344-derived secreted protein extracts for 5 h, and then probed as in (A). (C) HCT8 cells were infected with wild-type SL1344, SL1344ΔsopA or ΔsipA, or SL1344ΔSipA complemented with a vector expressing SipA (ΔSipA/pSipA) for 5 h, and then probed as in (A). Densitometry was analyzed by ImageJ and presented as relative to the untreated cells.

To facilitate understanding of the invention, a number of terms are defined below.

"PERP," "p53 apoptosis effector related to PMP-22" and "TP53 apoptosis effector" interchangeably refer to a tetraspan membrane protein originally identified as a transcriptional target of the p53 tumor suppressor (Davies et al., PERP expression stabilizes active p53 via modulation of p53-MDM2 interaction in uveal melanoma cells. *Cell Death Dis* 2, e136 (2011). Human PERP is exemplified by homo sapiens PERP amino acid sequence SEQ ID NO:02 (FIG. 10A) encoded by nucleotide sequence SEQ ID NO:03 (FIG. 10B) (NCBI Reference Sequence: NM_022121.4).

"P-glycoprotein," "P-gp," "MDR1 protein" are used interchangeably to refer to a membrane transport protein that promotes the expulsion of xenobiotics, which is a 170-kDa adenosine triphosphate (ATP)-dependent multispecific drug transporter. P-gp is encoded by MDR1, and is a multidrug resistance ATP-binding cassette (ABC) membrane transporter responsible for one aspect of the multi-drug resistance (MDR) phenotype in cancer cells (Krishna et al., *Curr Med Chem Anticancer Agents* 1, 163 (August 2001)). P-gp is exemplified by Homo sapiens (human) ABCB1 ATP-binding cassette, sub-family B (MDR/TAP), member 1, Gene ID: 5243. Several reports have linked the overexpression of P-gp to adverse treatment outcomes in many cancers, thereby identifying this MDR phenotype as an important biologic target for pharmacologic modulation (Krishna et al., *Curr Med Chem Anticancer Agents* 1, 163 (August 2001); Juliano et al., *Biochimica et biophysica acta* 455, 152 (Nov. 11, 1976)). Normal healthy tissues display baseline expression of P-gp, and it is believed to be an important protective mechanism against potentially toxic xenobiotics and to keep homeostasis. It is highly expressed in important pharmacological barriers, such as, placenta, brush border membrane of intestinal cells, the biliar canalicular membrane of hepatocytes, the lumenal membrane in proximal tubules of kidneys, and the epithelium that contributes to the blood-brain barrier (Gottesman, M. et al., Nat Rev Cancer. 2002 January; 2(1):48-58). Additionally, P-gp is expressed across different blood cells (Van de Ven, R. et al., J Leukoc Biol. 2009 November; 86(5):1075-87).

"Un-cleaved P-gp" refers to P-gp that has not been cleaved by caspase-3 (CASP3) to produce cleavage products that comprise an approximately 90 kDa P-gp cleavage product and/or an approximately 60 kDa P-gp cleavage product. Example 4 shows exemplary methods for determining the level of un-cleaved P-gp.

"Protein 53," "p53," "tumor protein 53" and "TP53" are interchangeably used to refer to a tumor suppressor protein that in humans is encoded by the TP53 gene.

A "variant" or "homolog" of a polypeptide sequence of interest or nucleotide sequence of interest, refers to a sequence that has at least 80% identity, including 80%, 81%, 82%, 83%, 84%, 85%, 86%, 87%, 88%, 89%, 90%, 91%, 92%, 93%, 94%, 95%, 96%, 97%, 98%, 99% and 100% identity with the polypeptide sequence of interest or nucleotide sequence of interest, respectively.

In one preferred embodiment, the variant has at least 95% identity to the sequence of interest, including 95%, 96%, 97%, 98%, 99%, and 100% identity with the sequence of interest.

"Identity" when in reference to 2 or more sequences (e.g., DNA, RNA, and/or protein sequences) refers to the degree of similarity between the 2 or more sequences, and is generally expressed as a percentage. Identity in amino acid or nucleotide sequences can be determined using Karlin and Altschul's BLAST algorithm (Proc. Natl. Acad. Sci. USA, 1990, 87, 2264-2268; Karlin, S. & Altschul, S F., Proc. Natl. Acad. Sci. USA, 1993, 90, 5873). Programs called BLASTN and BLASTX have been developed using the BLAST algorithm as a base (Altschul, S F. et al., J. Mol. Biol., 1990, 215, 403). When using BLASTN to analyze nucleotide sequences, the parameters can be set at, for example, score=100 and word length=12. In addition, when using BLASTX to analyze amino acid sequences, the parameters can be set at, for example, score=50 and word length=3. When using BLAST and the Gapped BLAST program, the default parameters for each program are used. Specific techniques for these analysis methods are the well known, e.g., on the website of the National Center for Biotechnology Information.

"Purify" and grammatical equivalents thereof when in reference to a desirable component (such as cell, protein, nucleic acid sequence, carbohydrate etc.) refer to the reduction in the amount of at least one undesirable component (such as cell, protein, nucleic acid sequence, carbohydrate, sialic acid-glycoprotein etc.) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in "enrichment" (i.e., an increase) in the amount of the desirable component relative to one or more undesirable components, resulting in a more concentrated form (relative to the starting material, such as the cell lysate and/or extracellular solution) of the desirable component "Cytotoxic" molecule refers any molecule that reduces proliferation and/or viability of a target cell, preferably, though not necessarily, killing the target cell. In a preferred embodiment, the cytotoxic molecule is an anti-cancer toxin.

"Anti-cancer toxin" and "anti-cancer cytotoxin" is a molecule that reduces proliferation of cancer cells and/or reduces viability of cancer cells and/or reduces tumor size and/or reduces tumor number and/or reduces metastasis and/or increases apoptosis of cancer cells. In preferred embodiments, anti-cancer toxins delay the onset of development of tumor development and/or reduce the number, weight, volume, and/or growth rate of tumors. Cytotoxins are exemplified by, without limitation, second messengers such as cAMP; Bacterial toxins such as the exemplary *Pertussis* toxin, Cholera toxin, and C3 exoenzyme; Lectins such as Ricin A (Engert et al. Blood. 1997 January 15; 89(2):403-10.). Also included are toxins exemplified by Topoisomerase inhibitors such as etoposide, Campothecin irinotecan, topotecan, anthracyclines (doxorubicine, daunorubicine); Microtubule inhibitors such as vincristine, vinblastine, vinorelbine, paclitaxel, docetaxel; Platinum containing compounds such as cisplatin, carboplatin, oxaloplatin, etc.; Alkylating agents such as cyclophosphamide, and ifosfamide; Antimetabolites such as methotrexate and mercaptoprine; Anti-estrogens such as tamoxifen and toremifene; Retinoids such as all trans-retinoic acid; and others such as Adriamycin, gemcitabine, and 5-fluoruracil.

A number of the above-mentioned toxins also have a wide variety of analogues and derivatives, including, but not limited to, cisplatin, cyclophosphamide, misonidazole, tirapazamine, nitrosourea, mercaptopurine, methotrexate, flurouracil, epirubicin, doxorubicin, vindesine and etoposide. Analogues and derivatives include $(CPA)_2Pt(DOLYM)$ and $(DACH)Pt(DOLYM)$ cisplatin, Cis-$(PtCl_2(4,7-H-5-methyl-7-oxo-)1,2,4(triazolo(1,5-a)pyrimidine)_2)$, $(Pt(cis-1,4-DACH)(trans-Cl_2)(CBDCA)) \cdot 1/2MeOH$ cisplatin, 4-pyridoxate diammine hydroxy platinum, $Pt(II) \cdot Pt(II)$ $(Pt_2(NHCHN(C(CH_2)(CH_3)))_4)$, 254-S cisplatin analogue, O-phenylenediamine ligand bearing cisplatin analogues, trans, cis-$(Pt(OAc)_2I_2(en))$, estrogenic 1,2-diarylethylenediamine ligand (with sulfur-containing amino acids and glutathione) bearing cisplatin analogues, cis-1,4-diaminocyclohexane cisplatin analogues, 5' orientational isomer of cis-$(Pt(NH_3)(4-aminoTEMP-O)\{d(GpG)\})$, chelating diamine-bearing cisplatin analogues, 1,2-diarylethyleneamine ligand-bearing cisplatin analogues, (ethylenediamine)platinum-(II) complexes, CI-973 cisplatin analogue, cis-diamminedichloroplatinum(II) and its analogues cis-1,1-cyclobutanedicarbosylato(2R)-2-methyl-1,4-butanediam-mineplatinum-(II) and cis-diammine(glycolato)platinum, cis-amine-cyclohexylamine-dichloroplatinum(II), gem-diphosphonate cisplatin analogues (FR 2683529), (meso-1,2-bis(2,6-dichloro-4-hydroxyplenyl)ethylenediamine) dichloroplatinum(II), cisplatin analogues containing a tethered dansyl group, platinum(II) polyamines, cis-(3H) dichloro(ethylenediamine)platinum(II), trans-diamminedichloroplatinum(II) and cis-$(Pt(NH_3)_2(N_3-cytosine)Cl)$, 3H-cis-1,2-diaminocyclohexanedichloroplatinum(II) and 3H-cis-1,2-diaminocyclohexane-malonatoplatinum (II), diaminocarboxylatoplatinum (EPA 296321), trans-(D,1)-1,2-diaminocyclohexane carrier ligand-bearing platinum analogues, aminoalkylaminoanthraquinone-derived cisplatin analogues, spiroplatin, carboplatin, iproplatin and JM40 platinum analogues, bidentate tertiary diamine-containing cisplatinum derivatives, platinum(H), platinum(IV), cis-diammine (1,1-cyclobutanedicarboxylato-)platinum(II) (carboplatin, JM8) and ethylenediamine-malonatoplatinum (II) (JM40), JM8 and JM9 cisplatin analogues, $(NPr4)_2((PtCL4) \cdot cis-(PtC12-(NH2Me)2))$, aliphatic tricarboxylic acid platinum complexes (EPA 185225), cis-dichloro(amino acid)(tert-butylamine)platinum-(II) complexes; 4-hydroperoxycylcophosphamide, acyclouridine cyclophosphamide derivatives, 1,3,2-dioxa- and oxazaphosphorinane cyclophosphamide analogues, C5-substituted cyclophosphamide analogues, tetrahydrooxazine cyclophosphamide analogues, phenyl ketone cyclophosphamide analogues, phenylketophosphamide cyclophosphamide analogues, ASTA Z-7557 cyclophosphamide analogues, 3-(1-oxy-2,2,6,6-tetramethyl-4-piperidinyl)cyclophosphamide, 2-oxobis(2-β-chloroethylamino)-4-,6-dimethyl-1,3,2-oxazaphosphorinane cyclophosphamide, 5-fluoro- and 5-chlorocyclophosphamide, cis- and trans-4-phenylcyclophosphamide, 5-bromocyclophosphamide, 3,5-dehydrocyclophosphamide, 4-ethoxycarbonyl cyclophosphamide analogues, arylaminotetrahydro-2H-1,3,2-oxazaphosphorine 2-oxide cyclophosphamide analogues, NSC-26271 cyclophosphamide analogues, benzo annulated cyclophosphamide analogues, 6-trifluoromethylcyclophosphamide, 4-methylcyclophosphamide and 6-methycyclophosphamide analogues; FCE 23762 doxorubicin derivative, annamycin, ruboxyl, anthracycline disaccharide doxorubicin analogue, N-(trifluoroacetyl)doxorubicin and 4'-O-acetyl-N-(trifluoroacetyl)-doxorubicin, 2-pyrrolinodoxorubicin, disaccharide doxorubicin analogues, 4-demethoxy-7-O-(2,6-dideoxy-4-O-(2,3,6-trideoxy-3-amino-α-L-lyxo-hexopyranosyl)-α-L-lyxo-hexopyranosyl) adriamicinone doxorubicin disaccharide analog, 2-pyrrolinodoxorubicin, morpholinyl doxorubicin analogues, enaminomalonyl-β-alanine doxorubicin derivatives, cephalosporin doxorubicin derivatives, hydroxyrubicin, methoxymorpholino doxorubicin derivative, (6-maleimidocaproyl) hydrazone doxorubicin derivative, N-(5,5-diacetoxypent-1-yl) doxorubicin, FCE 23762 methoxymorpholinyl doxorubicin derivative, N-hydroxysuccinimide ester doxorubicin derivatives, polydeoxynucleotide doxorubicin derivatives, morpholinyl doxorubicin derivatives (EPA 434960), mitoxantrone doxorubicin analogue, AD198 doxorubicin analogue, 4-demethoxy-3'-N-trifluoroacetyldoxorubicin, 4'-epidoxorubicin, alkylating cyanomotpholino doxorubicin derivative, deoxydihydroiodooxorubicin (EPA 275966), adriblastin, 4'-deoxydoxorubicin, 4-demethyoxy-4'-o-methyldoxorubicin, 3'-deamino-3'-hydroxydoxorubicin, 4-demethyoxy doxorubicin analogues, N-L-leucyl doxorubicin derivatives, 3'-deamino-3'-(4-methoxy-1-piperidinyl) doxorubicin derivatives (U.S. Pat. No. 4,314,054), 3'-deamino-3'-(4-mortholinyl) doxorubicin derivatives (U.S. Pat. No. 4,301,277), 4'-deoxydoxorubicin and 4'-o-methyldoxombicin, aglycone doxorubicin derivatives, SM 5887, MX-2, 4'-deoxy-13(S)-dihydro-4'-iododoxorubicin (EP 275966), morpholinyl doxorubicin derivatives (EPA 434960), 3'-deamino-3'-(4-methoxy-1-piperidinyl) doxorubicin derivatives (U.S. Pat. No. 4,314,054), doxorubicin-14-valerate, morpholinodoxorubicin (U.S. Pat. No. 5,004,606), 3'-deamino-3'-(3'-cyano-4"-morpholinyl doxorubicin; 3'-deamino-3'-(3"-cyano-4"-morpholinyl)-13-dihydoxorubicin; (3'-deamino-3'-(3"-cyano-4"-morpholinyl) daunorubicin; 3'-deamino-3'-(3"-cyano-4"-morpholinyl)-3-dihydrodaunontbicin; and 3'-deamino-3'-(4"-morpholinyl-5-iminodoxorubicin and derivatives (U.S. Pat. No. 4,585,859), 3'-deamino-3'-(4-methoxy-1-piperidinyl) doxorubicin derivatives (U.S. Pat. No. 4,314,054) and 3-deamino-3-(4-morpholinyl) doxorubicin derivatives (U.S. Pat. No. 4,301,277); 4,5-dimethylmisonidazole, azo and azoxy misonidazole derivatives; RB90740; 6-bromo and 6-chloro-2,3-dihydro-1,4-benzothiazines nitrosourea derivatives, diamino acid nitrosourea derivatives, amino acid nitrosourea derivatives, 3',4'-didemethoxy-3',4'-dioxo-4-deoxypodophyllotoxin nitrosourea derivatives, ACNU, tertiary phosphine oxide nitrosourea derivatives, sulfamerizine and sulfamethizole nitrosourea derivatives, thymidine nitrosourea analogues, 1,3-bis(2-chloroethyl)-1-nitrosourea, 2,2,6,6-tetramethyl-1-oxopiperidiunium nitrosourea derivatives (U.S.S.R. 1261253), 2- and 4-deoxy sugar nitrosourea derivatives (U.S. Pat. No. 4,902,791), nitroxyl nitrosourea derivatives (U.S.S.R. 1336489), fotemustine, pyrimidine (II) nitrosourea derivatives, CGP 6809, B-3839, 5-halogenocytosine nitrosourea derivatives, 1-(2-chloroethyl)-3-isobutyl-3-(β-maltosyl)-1-nitrosourea, sulfur-containing nitrosoureas, sucrose, 6-((((2-chloroethyl)nitrosoamino-)carbonyl)amino)-6-deoxysucrose (NS-1C) and 6'((((2-chloroethyl)nitrosoamino)carbonyl)amino)-6'-deoxysucrose (NS-1D) nitrosourea derivatives, CNCC, RFCNU and chlorozotocin, CNUA, 1-(2-chloroethyl)-3-isobutyl-3-(β-maltosyl)-1-nitrosourea, choline-like nitrosoalkylureas, sucrose nitrosourea derivatives (JP 84219300), sulfa drug nitrosourea analogues, DONU, N,N'-bis (N-(2-chloroethyl)-N-nitrosocarbamoyl)cystamine (CNCC), dimethylnitrosourea, GANU, CCNU, 5-aminomethyl-2'-deoxyuridine nitrosourea analogues, TA-077, gentianose nitrosourea derivatives (JP 82 80396), CNCC, RFCNU, RPCNU AND chlorozotocin (CZT), thiocolchicine nitrosourea analogues, 2-chloroethylnitrosourea, ACNU, (1-(4-amino-2-methyl-5-pyrimidinyl) methyl-3-(2-chloroethyl)-3-nitrosourea hydrochloride), N-deacetylmethyl thiocolchicine nitrosourea analogues, pyridine and piperidine nitrosourea derivatives, methyl-CCNU, phensuzimide nitrosourea derivatives, ergoline nitrosourea derivatives, glucopyranose nitrosourea derivatives (JP 78 95917), 1-(2-chloroethyl)-3-cyclohexyl-1-nitrosourea, 4-(3-(2-chloroethyl)-3-nitrosoureid-o)-cis-cyclohexanecarboxylic acid, RPCNU (ICIG 1163), IOB-252, 1,3-bis(2-chloroethyl)-1-nitrosourea (BCNU), 1-tetrahydroxycyclopentyl-3-nitroso-3-(2-chloroethyl)-urea (U.S. Pat. No. 4,039,578), d-1-1-(β-chloroethyl)-3-(2-oxo-3-hexahydroazepinyl)-1-nitrosourea (U.S. Pat. No. 3,859,277) and gentianose nitrosourea derivatives (JP 57080396); 6-S-aminoacyloxymethyl mercaptopurine derivatives, 6-mercaptopurine (6-MP), 7,8-polymethyleneimidazo-1,3,2-diazaphosphorines, azathioprine, methyl-D-glucopyranoside mercaptopurine derivatives and s-alkynyl mercaptopurine derivatives; indoline ring and a modified ornithine or glutamic acid-bearing methotrexate derivatives, alkyl-substituted benzene ring C bearing methotrexate derivatives, benzoxazine or benzothiazine moiety-bearing methotrexate derivatives, 10-deazaaminopterin analogues, 5-deazaaminopterin and 5,10-dideazaaminopterin methotrexate analogues, indoline moiety-bearing methotrexate derivatives, lipophilic amide methotrexate derivatives, L-threo-(2S,4S)-4-fluoro-glutamic acid and DL-3,3-difluoroglutamic acid-containing methotrexate analogues, methotrexate tetrahydroquinazoline analogue, N-(ac-aminoacyl) methotrexate derivatives, biotin methotrexate derivatives, D-glutamic acid or D-erythrou, threo-4-fluoroglutamic acid methotrexate analogues, β,γ-methano methotrexate analogues, 10-deazaaminopterin (10-EDAM) analogue, γ-tetrazole methotrexate analogue, N-(L-α-aminoacyl) methotrexate derivatives, meta and ortho isomers of aminopterin, hydroxymethylmethotrexate (DE 267495), γ-fluoromethotrexate, polyglutamyl methotrexate derivatives, gem-diphosphonate methotrexate analogues (WO 88/06158), α- and γ-substituted methotrexate analogues, 5-methyl-5-deaza methotrexate analogues (U.S. Pat. No. 4,725,687), N.delta.-acyl-N α-(4-amino-4-deoxypteroyl)-L-ornithine derivatives, 8-deaza methotrexate analogues, acivicin methotrexate analogue, polymeric platinol methotrexate derivative, methotrexate-γ-dimyristoylphophatidylethanolamine, methotrexate polyglutamate analogues, poly-γ-glutamyl methotrexate derivatives, deoxyuridylate methotrexate derivatives, iodoacetyl lysine methotrexate analogue, 2,.omega.-diaminoalkanoid acid-containing methotrexate analogues, polyglutamate methotrexate derivatives, 5-methyl-5-deaza analogues, quinazoline methotrexate analogue, pyrazine methotrexate analogue, cysteic acid and homocysteic acid methotrexate analogues (U.S. Pat. No. 4,490,529), γ-tert-butyl methotrexate esters, fluorinated methotrexate analogues, folate methotrexate analogue, phosphonoglutamic acid analogues, poly (L-lysine) methotrexate conjugates, dilysine and trilysine methotrexate derivates, 7-hydroxymethotrexate, poly-γ-glutamyl methotrexate analogues, 3',5'-dichloromethotrexate, diazoketone and chloromethylketone methotrexate analogues, 10-propargylaminopterin and alkyl methotrexate homologs, lectin derivatives of methotrexate, polyglutamate methotrexate derivatives, halogentated methotrexate derivatives, 8-alkyl-7,8-dihydro analogues, 7-methyl methotrexate derivatives and dichloromethotrexate, lipophilic methotrexate derivatives and 3',5'-dichloromethotrexate, deaza amethopterin analogues, MX068 and cysteic acid and homocysteic acid methotrexate analogues (EPA 0142220); N3-alkylated analogues of 5-fluorouracil, 5-fluorouracil derivatives with 1,4-oxaheteroepane moieties, 5-fluorouracil and nucleoside analogues, cis- and trans-5-fluoro-5,6-dihydro-6-alkoxyuracil, cyclopentane 5-fluorouracil analogues, A-OT-fluorouracil, N4-trimethoxybenzoyl-5'-deoxy-5-fluorocytidine and 5'-deoxy-5-fluorouridine, 1-hexylcarbamoyl-5-fluorouracil, B-3839, uracil-1-(2-tetrahydrofuryl)-5-fluorouracil, 1-(2'-deoxy-2'-fluoro-β-D-arabinofuranosyl)-5-fluorouracil, doxifluridine, 5'-deoxy-5-fluorouridine, 1-acetyl-3-O-toluyl-5-fluorouracil, 5-fluorouracil-m-formylbenzene-sulfonate (JP 55059173), N'-(2-furanidyl)-5-fluorouracil (JP 53149985)

and 1-(2-tetrahydrofuryl)-5-fluorouracil (JP 52089680); 4'-epidoxorubicin; N-substituted deacetylvinblastine amide (vindesine) sulfates; and Cu(II)-VP-16 (etoposide) complex, pyrrolecarboxamidino-bearing etoposide analogues, 40-amino etoposide analogues, γ-lactone ring-modified arylamino etoposide analogues, N-glucosyl etoposide analogue, etoposide A-ring analogues, 4'-deshydroxy-4'-methyl etoposide, pendulum ring etoposide analogues and E-ring desoxy etoposide analogues.

"Nanoparticle" refers to a particle of a solid (such as a metal, polymer, oxide, etc.) having one or more dimensions of approximately 100 nm or less. Enablement: generic methods for "linking" (i.e., "conjugating") molecules (such as chemotherapeutic agent, antibiotic agent, antifungal agent, antiparasitic agent, antiviral agent, SipA, etc.) to nanoparticles for drug delivery to tissue (such as cancer tissue), are known in the art (e.g., U.S. Pat. Nos. 8,318,208, 8,318,211, 8,246,968, 8,193,334, 8,063,131, 7,727,554, 7,563,457, 7,550,441, 7,550,282, 7,387,790, 7,348,030, 5,718,919, 5,503,723, 5,429,824; U.S. Patent Publication No. US 2012/0302516, WO 2008/151049) including gold nanoparticles (e.g., U.S. Pat. No. 8,323,694). Exemplary methods for conjugating SipA to gold nanoparticles are described herein in Examples 1, 5 and 7.

"Operably conjugated" and "operably linked" when in reference to the linkage between two molecules, such as the linkage between a nanoparticle and another molecules (such as SipA, cytotoxin, chemotherapeutic agent, antibiotic agent, antifungal agent, antiparasitic agent, antiviral agent, etc.) means that the molecules are linked such that each molecule performs its intended and/or biological function (e.g., SipA reduces the level of expression of P-gp in cells and/or reduces the level of functional un-cleaved P-gp in cells and/or increases the level of expression of PERP, etc.). Linkage may be direct, indirect, non-covalent, covalent, etc. In a preferred embodiment, linkage between nanoparticles and proteins is covalent to reduce protein dissociation or aggregation.

The terms "specifically binds" and "specific binding" when made in reference to the binding of two molecules (e.g. antibody to an antigen), etc., refer to an interaction of the two molecules that is dependent upon the presence of a particular structure on one or both of the molecules. For example, if an antibody is specific for epitope "A" on the molecule, then the presence of a protein containing epitope A (or free, unlabeled A) in a reaction containing labeled "A" and the antibody will reduce the amount of labeled A bound to the antibody.

"Antibody" refers to an immunoglobulin (e.g., IgG, IgM, IgA, IgE, IgD, etc.).

"Antigen-binding portion" of an antibody refers to a fragment of the antibody that specifically binds to an antigen. "Antigen-binding portion" includes a "variable domain" (also referred to as the "$F_V$ region") for binding to antigens. More specifically, variable loops, three each on the light ($V_L$) and heavy ($V_H$) chains are responsible for binding to the antigen. These loops are referred to as the "complementarity determining regions" ("CDRs") and "idiotypes." "Antigen-binding portion" includes the Fab region, F(ab')2 fragment, pFc' fragment, and Fab' fragments. The "Fab region" and "fragment, antigen binding region," interchangeably refer to portion of the antibody arms of the immunoglobulin "Y" that function in binding antigen. The Fab region is composed of one constant and one variable domain from each heavy and light chain of the antibody. Methods are known in the art for the construction of Fab expression libraries (Huse et al., Science, 246:1275-1281 (1989)) to allow rapid and easy identification of monoclonal Fab fragments with the desired specificity. In another embodiment, Fc and Fab fragments can be generated by using the enzyme papain to cleave an immunoglobulin monomer into two Fab fragments and an Fc fragment. The enzyme pepsin cleaves below the hinge region, so a "F(ab')2 fragment" and a "pFc' fragment" is formed. The F(ab')2 fragment can be split into two "Fab' fragments" by mild reduction.

The "Fc" and "Fragment, crystallizable" region interchangeably refer to portion of the base of the immunoglobulin "Y" that function in role in modulating immune cell activity. The Fc region is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils. In an experimental setting, Fc and Fab fragments can be generated in the laboratory by cleaving an immunoglobulin monomer with the enzyme papain into two Fab fragments and an Fc fragment.

"Cyclic-arginine-glycine-aspartic acid," "cRGD," "cGRGDdvc" and "LXW7" interchangeably refer to an arginine-glycine-aspartic acid peptide cyclized by a disulfide bond and with a built-in handle at the carboxyl terminus.

"Cancer cell" refers to a cell undergoing early, intermediate or advanced stages of multi-step neoplastic progression as previously described (Pitot et al., Fundamentals of Oncology, 15-28 (1978)). This includes cells in early, intermediate and advanced stages of neoplastic progression including "pre-neoplastic cells (i.e., "hyperplastic cells and dysplastic cells), and neoplastic cells in advanced stages of neoplastic progression of a dysplastic cell. "Cancer" includes cells that may or may not be metastatic, and is exemplified by ovarian cancer, breast cancer, lung cancer, prostate cancer, cervical cancer, pancreatic cancer, colon cancer, stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia. In a particularly preferred embodiment, the cancer comprises one or more of a colon cancer (see Example 2), colorectal cancer, gastro-intestinal cancer, breast cancer (see Example 3), bladder cancer (see Example 3), kidney cancer, leukemia, brain cancer, sarcoma, astrocytoma, acute myelogenous leukemia (AML), and diffuse large B-lymphoma.

"Symptom" is a sign of disease. Cancer symptoms include, but are not limited to, weight loss, fever, fatigue, bleeding or discharge (lung, colon, rectal, cervix endometrium, bladder, kidney and/or breast cancers), sores that do not heal (skin and/or oral cancers), white patches inside the mouth or white spots on the tongue (leukoplakia in mouth cancer), thickening or lumps (breast, testicle, and/or lymph node cancers), tumor size, tumor rate of growth, indigestion or trouble swallowing (esophagus, stomach, and/or throat cancers), changes in size or color of moles (melanoma), cough or hoarseness (lung, voice box and/or thyroid gland cancers). Multiple sclerosis symptoms include, but are not limited to, numbness or weakness in one or more limbs, partial or complete loss of central vision, usually in one eye, often with pain during eye movement (optic neuritis), double vision or blurring of vision, tingling or pain in parts of the body, electric-shock sensations that occur with certain head movements, tremor, lack of coordination or unsteady gait, slurred speech, fatigue and/or dizziness. Autoimmune disease symptoms include, but are not limited to, extreme fatigue, muscle and joint pain, muscle weakness, swollen glands, inflammation, susceptibility to infections, sleep disturbances, weight loss or gain, low blood sugar, blood pressure changes, *Candida* yeast infections, allergies, digestive problems such as abdominal pain, bloating, tenderness, heartburn, cramps, constipation, diarrhea and excessive gas ("leaky gut syndrome"), anxiety and depression, memory problems, thyroid problems (hypothyroidism and/or hyperthyroidism) that can manifest as low body temperature and excessive hair loss, re-current headaches, low grade fevers, and/or re-current miscarriage. Human Immunodeficiency Virus (HIV) infection symptoms include, but are not limited to, fatigue, diarrhea, nausea, vomiting, fever, chills, night sweats, muscle aches, sore throat, swollen lymph nodes, ulcers in the mouth, wasting syndrome at late stages, and/or opportunistic infections which occur in patients with a damaged immune system.

"Non-cancerous cell" refers to a cell that is not a cancer cell, such as a cell that is not undergoing early, intermediate or advanced stages of multi-step neoplastic progression.

A cell that is "resistant to a cytotoxin" refers to a cell whose rate of growth is not substantially reduced in the presence of the cytotoxin as compared to in the absence of the cytotoxin.

A "control" sample or cell refers to a sample or cell used for comparing to another sample or cell by maintaining the same conditions in the control and other samples or cells, except in one or more particular variable in order to infer a causal significance of this varied one or more variable on a phenomenon. For example, a non-cancerous cell is a control cell vis-à-vis a cancer cell. In another example, a cell that is not infected with a virus is a control cell vis-à-vis a cell that is infected with the virus. Also, for example, a "positive control sample" is a control sample in which the phenomenon is expected to occur. For example, a "negative control sample" is a control sample in which the phenomenon is not expected to occur.

Cells that "overexpress" a protein and/or nucleotide sequence refer to cells that produce a higher level of the protein and/or nucleotide sequence compared to a control cell.

A "subject" includes any multicellular animal, preferably a "mammal." Mammalian subjects include humans, non-human primates, murines, ovines, bovines, ruminants, lagomorphs, porcines, caprines, equines, canines, felines, ayes, etc.). Thus, mammalian subjects are exemplified by mouse, rat, guinea pig, hamster, ferret and chinchilla.

A subject "in need" of reducing one or more symptoms of a disease includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable).

A subject "at risk" for disease refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

The terms "reduce," "inhibit," "diminish," "suppress," "decrease," and grammatical equivalents (including "lower," "smaller," etc.) when in reference to the level of any molecule (e.g., amino acid sequence such as P-gp or PERP, and nucleic acid sequence such as a sequence encoding P-gp or PERP, antibody, etc.), cell, and/or phenomenon (e.g., level of expression of a gene such as the gene encoding P-gp or PERP, disease symptom, cell proliferation, cell viability, tumor size, tumor number, level of binding of two molecules, enzyme activity, biological activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

The terms "increase," "elevate," "raise," and grammatical equivalents (including "higher," "greater," etc.) when in reference to the level of any molecule (e.g., amino acid sequence such as P-gp or PERP, and nucleic acid sequence such as a sequence encoding P-gp or PERP, antibody, etc.), cell, and/or phenomenon (e.g., level of expression of a gene such as the gene encoding P-gp or PERP, disease symptom, cell proliferation, cell viability, tumor size, tumor number, level of binding of two molecules, enzyme activity, biological activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

The term "not substantially reduced" when in reference to the level of any molecule (e.g., amino acid sequence such as P-gp or PERP, and nucleic acid sequence such as a sequence encoding P-gp or PERP, antibody, etc.), cell, and/or phenomenon (e.g., level of expression of a gene such as the gene encoding P-gp or PERP, disease symptom, cell proliferation, cell viability, tumor size, tumor number, level of binding of two molecules, enzyme activity, biological activity, etc.) in a first sample (or in a first subject) relative to a second sample (or relative to a second subject), means that the quantity of molecule, cell and/or phenomenon in the first sample (or in the first subject) is from 91% to 100% of the quantity in the second sample (or in the second subject).

The terms "alter" and "modify" when in reference to the level of any molecule and/or phenomenon refer to an increase and/or decrease.

SUMMARY OF THE INVENTION

The invention provides a method for reducing one or more symptoms of cancer in a mammalian subject in need thereof, comprising administering to said subject a composition comprising purified SipA. In one embodiment, said SipA is operably conjugated to a nanoparticle. In another embodiment, said cancer comprises cancer cells resistant to at least one cytotoxin. In yet another embodiment, said cancer comprises cancer cells that overexpress one or more of P-gp and p53 compared to a control cell. In a further embodiment, the method optionally further comprises administering to said subject one or more cytotoxin. In one embodiment, said SipA is administered in an amount that is effective in one or more of a) reducing the level of expression of P-gp in cells of said cancer, b) reducing the level of un-cleaved P-gp in cells of said cancer, and c) increasing the level of expression of PERP in cells of said cancer. In yet another embodiment, said method further comprises determining the level of expression of P-gp in cells of said cancer. In a particular embodiment, said SipA is operably conjugated to a cytotoxin. In another embodiment, said SipA is operably conjugated to a targeting agent that specifically binds to cells of said cancer. In an alternative embodiment, said targeting agent comprises an antibody, or an antigen-binding portion thereof. In one preferred embodiment, said targeting agent comprises cyclic-arginine-glycine-aspartic acid (cRGD) peptide. In an alternative embodiment, said targeting agent comprises folic acid.

The invention further provides a method for reducing one or more symptoms of a disease in a mammalian subject in need thereof, wherein said disease is associated with cells that overexpress one or more of P-gp and p53, said method comprising administering to said subject a composition comprising purified SipA, wherein said SipA is in an amount that is effective in one or more of a) reducing the level of expression of P-gp in said cells, b) reducing the level of un-cleaved P-gp in said cells, and c) increasing the level of expression of PERP in said cells. In one embodiment, said disease is selected from the group consisting of cancer, multiple sclerosis, autoimmune disease, and Human Immunodeficiency Virus (HIV) infection.

Also provided by the invention is a method comprising administering to a mammalian cell a composition comprising purified SipA, wherein said SipA is in an amount that is effective in one or more of a) reducing the level of expression of P-gp in said cell, b) reducing the level of un-cleaved P-gp in said cell, and c) increasing the level of expression of PERP in said cell. In one embodiment, said cell overexpresses one or more of said P-gp and of p53 compared to a control cell. In another embodiment, said cell that overexpresses said P-gp is selected from the group consisting of cancer cell and non-cancerous cell. In one embodiment, said cell is in vitro or in vivo. In yet another embodiment, said non-cancerous cell comprises a lymphocyte cell. In a further embodiment, said non-cancerous cell comprises an intestinal epithelial cell.

The invention further provides a nanoparticle comprising one or more purified SipA.

The invention additionally provides a composition comprising any one or more of the nanoparticles described herein, and at least one pharmaceutically acceptable diluent or excipient.

The invention also provides a method for increasing apoptosis of cancer cells in a mammalian subject in need thereof, comprising administering to said subject a composition comprising purified SipA.

BRIEF DESCRIPTION OF THE INVENTION

The invention provides the seminal discovery that a type III secreted effector protein, SipA (Salmonella invasion protein A), isolated from the enteric pathogen Salmonella enterica serovar typhimurium has the combined role of functionally down-regulating MDR1 (or P-glycoprotein), and triggering pathways that stabilize active p53, ultimately driving apoptotic responses.

The invention also provides the surprising discovery of a link between a microorganism that is targeted specifically to tumors, and the regulation of multidrug resistance transporters. Data herein demonstrate that colonization of human colon cancer cell lines (that overexpress P-gp) by wild-type S. Typhimurium led to a profound functional decrease and loss of protein expression in the multidrug resistance protein transporter, P-gp (5).

In particular, the invention provides the discovery that SipA presents a major advance with respect to previously developed small molecule entities that target MDR and/or p53 drug-based strategies because it a molecule derived from a pathogenic microorganism evolutionary programmed to biologically engage epithelial cells and is also stable in hostile microenvironments, such as cancers.

The invention also provides the discovery that expression of P-gp and activation of apoptosis (programmed cell death) share an inverse relationship. P-gp protein expression plays a major role in promoting cell survival, where it functions primarily as an anti-apoptotic molecule presumably by pumping out enzymes critical to catalyzing the apoptotic cascade. Accordingly, by functionally down-regulating P-gp, the invention's nanoparticle possesses the additional advantage of driving tumors to become more sensitive to apoptosis. Improved treatment that targets apoptosis is based on two key observations: 1) Many of the changes contributing to cancer development also diminish the ability of cells to undergo apoptosis (9). When this death process is inhibited, damaged or defective cells that ordinarily would be eliminated instead accumulate and cause significant pathologic problems; and ii) a variety of studies have demonstrated that apoptosis is a frequent outcome of effective therapy (9). Consequently, one of the invention's advantages is to facilitate apoptosis in neoplastic cells.

The invention further provides the surprising and serendipitous discovery that the S. Typhimurium effector, SipA, promotes the production of PERP (p53 apoptosis effector related to—PMP-22) in epithelial cells, and that SipA enhances and stabilizes p53 activity.

Data herein demonstrate that SipA does not need to enter the epithelial cell cytosol to stimulate signal transduction pathways but, rather, functions extracellularly at the epithelial cell surface, where it engages a specific receptor. This finding is a paradigm-shifting surprising discovery since it challenges the long-held view that type III secretion system effector proteins must be directly delivered into host cells from bacterial cells to engage signal transduction pathways.

The invention also provides a drug nanocarrier that addresses the shortcomings of traditional chemotherapeutic treatment, and that targets multidrug-resistant tumors while simultaneously stabilizing active p53, a tumor suppressor protein. The design of the novel chemotherapeutic and SipA co-conjugated drug delivery system capitalizes the unique chemical and physical properties of the nanoparticle, biochemical functional activities of SipA, and pharmaceutical effectiveness of chemotherapeutic agents (such as the FDA approved doxorubicin). The invention's nanoparticle compositions establish a new paradigm in chemotherapeutic drug delivery, as treatment methods using this nanocarrier offer unprecedented therapeutic potential by drastically improving efficacy while minimizing drug associated side effects. The invention's compositions and methods therefore will profoundly change the way disease, and particularly cancer, is treated.

DETAILED DESCRIPTION OF THE INVENTION

The invention provides compositions and methods for reducing one or more symptoms of disease by administering compositions comprising a polypeptide sequence having at least 95% identity to SipA (SEQ ID NO:01). The invention's compositions and methods are particularly advantageous in reducing symptoms of diseases that are associated with overexpression of P-gp and/or p53. The invention's compositions and methods are useful in reducing cancer symptoms and/or cancer multidrug resistance (MDR). The invention is further described under (1) Salmonella enterica serovar Typhimurium (S. Typhimurium) interactions with host cells, (2) Salmonella T3SS effector protein (SipA), (3) Methods for reducing disease symptoms, and (4) SipA conjugated to nanoparticles.

1. Salmonella Enterica Serovar Typhimurium (S. Typhimurium) Interactions with Host Cells Bacterial pathogens have been investigated as therapeutic agents for tumors for over 150 years (1). As an example, Salmonella enterica serovar Typhimurium (S. Typhimurium) is a facultative enteric pathogen that causes food poisoning in humans resulting in gastroenteritis. This pathogen can also selectively grow in tumors following systemic administration and is able to modulate numerous biochemical pathways across a broad spectrum of cell types (i.e., gut, kidney, lung, macrophages) (2, 3) (4). Therefore, the invention's compositions and methods that harness these traits afford unique opportunities to overcome many of the delivery barriers that hinder conventional chemotherapeutics.

S. typhimurium initiates infection and controls the fate of the host cells by invading enterocytes predominantly located within the distal ileum, and has evolved the use of a needle-like structure, known as the type III secretion system to guide its pathogenesis (5). By way of this sophisticated secretion system, numerous Salmonella effector proteins are secreted from the bacterium and then are translocated into the target cell cytosol. Such secreted effectors have high potential as therapeutic agents because they have co-evolved with the host and are extremely adept at interacting with host cell proteins involved in the modulation numerous signaling transduction pathways that are common targets fundamental in the development of therapeutics of inflammatory diseases and cancer (4, 5).

The inventors investigated *Salmonella*-host cell interactions with regard to the expression and functionality of P-gp. Recent reports have linked the overexpression of P-gp to adverse treatment outcomes in many cancers, thereby identifying this MDR phenotype as an important biologic target for pharmacologic modulation (6, 7). The inventors' prior studies revealed that colonization of *S. Typhimurium* with human colon cancer cell lines that overexpress P-gp leads to a profound functional decrease and loss of protein expression in P-gp (8). There are also reports documenting the ability of *S. Typhimurium* to target and selectively grow in tumors (accumulating 2000-fold more in tumors than in other healthy organs (3)).

2. *Salmonella* T3SS Effector Protein (SipA)

Data herein identify that the *Salmonella* type III secretion effector, SipA, is responsible for the effect of P-gp down-regulation, and show that the *Salmonella Typhimurium* secreted effector protein, SipA, can selectively and robustly down regulate P-gp. Data herein shows that SipA modulates P-gp expression in several cancers that are known to over-express P-gp, such as colon, kidney, and breast cancer. The invention exploits this virulence determinant in the development of a novel strategy aimed at reducing (including reversing) multidrug resistance in tumors. Since SipA is a stable molecule that has co-evolved with the human host, this virulence factor represents a major advance with respect to previously developed small molecule entities that target MDR.

Exploiting these observations, the invention further provides a therapeutic application where the inventors engineered a SipA conjugated gold nanoparticle (SipA-AuNP) system, which mimics the ability to reverse multidrug resistance. Using this system, the inventors found that a AuNP conjugated with SipA can reduce P-gp expression in cancer cells at a SipA dose that is nearly 500 times lower than free unbound SipA. The inventors also demonstrate that the SipA-AuNP, when used in conjunction with the exemplary potent cancer chemotherapeutic drug doxorubicin suppresses tumor growth.

"SipA" and "*Salmonella* T3SS effector protein" are used interchangeably to refer to a protein produced by *Salmonella*, as exemplified by the amino acid sequence SEQ ID NO:01 of *Salmonella enterica* subsp. *enterica* serovar Typhimurium str. SL1344 (GenBank: AAA86618.1) (FIG. 7) encoded by the DNA sequence (Locus taq) SL1344_2861 of the *Salmonella enterica* subsp. *enterica* serovar Typhimurium str. SL1344, complete genome sequence (NCBI Reference Sequence: NC_016810.1).

Several biological activities have been identified for SipA. For example, SipA has been shown to participate in actin polymerization and bacterial invasion (Zhou D et al., Science. 1999 Mar. 26; 283(5410):2092-5; Schumberger M C. Et al., Mol Microbiol. 2007 August; 65(3):741-60). SipA has been shown to be involved in pro-inflammatory responses, such as neutrophil recruitment (Wall, D. et al., Cell Microbiol. 2007 September; 9(9):2299-313; Silva M., et al., *Am J Physiol Gastrointest Liver Physiol.* 2004 June; 286(6):G1024-31; Criss A K. et al., *J Biol Chem.* 2001 Dec. 21; 276(51):48431-9; and Lee C A. et al., *Proc Natl Acad Sci USA.* 2000 Oct. 24; 97(22):12283-8), activation of the NOD1/NOD2 signaling pathway (Keestra A M, et al., *MBio.* 2011 Dec. 20; 2(6)), and CXC chemokine expression (through p38MAPK and JUN pathways (Figueiredo J F. et al., *Microbes Infect.* 2009 February; 11(2):302-10). SipA has also been shown to be active in Mrp2 up-regulation and HXA3 axis (Pazos M, et al., *J Immunol.* 2008 Dec. 1; 181(11):8044-52; Agbor, T., et al., *Cell Microbiol.* 2011 December; 13(12):2007-21; and Mrsny R J. et al., *Proc Natl Acad Sci USA.* 2004 May 11; 101(19):7421-6).

The active sites in SipA that are associated with its several biological functions have also been mapped. For example, the active sites for SipA actin polymerization and bacterial invasion activity are located in the carboxyl-terminal (ABD domain amino acid 446-685 of SEQ ID NO:01) (Galkin, V. et al., Nature Structural Biology 9, 518-521 (2002)). The active sites for SipA actin polymerization and bacterial invasion are also located in the central region of SipA (amino acid 105-446 of SEQ ID NO:01), including the F1 (amino acid 170-271 of SEQ ID NO:01) which is required for initiation of SipA focus formation and cooperates with the ABD domain, and the F2 (amino acid 280-394 of SEQ ID NO:01) which enhances focal accumulation of SipA presumably via intermolecular SipA-SipA interactions (Schumberger M C. Et al., Mol Microbiol. 2007 August; 65(3):741-60). The active sites for SipA actin polymerization and bacterial invasion are also located in the N-terminal SipA region (amino acid 1-105 of SEQ ID NO:01) which mediates TTSS-1 transport (Bronstein, P. et al., Bacteriol. 2000 December; 182(23): 6638-6644).

The active site for SipA neutrophil recruitment activity are located in SipAa3 (amino acid 294-424 of SEQ ID NO:01) which is a 131-amino-acid region (Wall, D. et al., *Cell Microbiol.* 2007 September; 9(9):2299-313).

3. Methods for Reducing Disease Symptoms

In one embodiment, the invention provides a method for reducing one or more symptoms of a disease in a mammalian subject in need thereof (including at risk for disease), wherein the disease is associated with cells that overexpress one or more of P-gp and p53, the method comprising administering to the subject a composition comprising SipA, and/or polypeptide sequence having at least 95% identity to SipA (SEQ ID NO:01), wherein SipA (and/or the polypeptide sequence) is in an amount that is effective in one or more of a) reducing the level of expression of P-gp in the cells, b) reducing the level of functional un-cleaved P-gp in the cells, and c) increasing the level of expression of PERP in the cells. In one embodiment, SipA and/or the polypeptide sequence having at least 95% identity to SipA is purified.

Thus in one embodiment, data in Examples 2 and 3 demonstrated that SipA is effective in reducing the level of expression of P-gp in the cells.

In another embodiment, Example 4 shows that SipA reduces the level of functional un-cleaved P-gp by increasing the level of cleavage of P-gp by caspase-3 (CASP3), thus increasing the level of P-gp cleavage products that comprise the approximately 90 kDa P-gp cleavage product and/or the approximately 60 kDa P-gp cleavage product.

In a further embodiment, SipA increases the level of expression of PERP in cells. PERP is a tetraspan membrane protein originally identified as a transcriptional target of the p53 tumor suppressor (10). P53 regulates the cell cycle and, thus, functions as a tumor suppressor that is involved in preventing cancer. As such, p53 has been described as "the guardian of the genome", referring to its role in conserving stability by preventing genome mutation. Fundamental to the tumor-suppressor role of p53 is the ability to engage in apoptosis. This notion is strongly supported by studies revealing the presence of p53 mutations in over half of human cancers (11, 12), and the compromised p53 activity (by other mechanisms) in the majority of other cancers (12).

Studies investigating the interaction of SipA with the surface epithelial cells have been carried out (13, 14). The inventors used a split-ubiquitin based yeast-two hybrid analysis system (Dualsystems Biotech) with full length SipA as bait and a human cancer colon mRNA-based library as prey, to identify PERP, a p53 induced apoptotic effector, as a SipA interacting partner. Not only does SipA bind to PERP at epithelial surfaces, but it also up-regulates the protein expression of PERP in human colonic cancers in vitro. While an understanding of the mechanism is not necessary, and without limiting the invention to any particular mechanism, and although the precise function of PERP in eliciting an apoptotic response remains unknown, initial reports indicate that PERP expression causes nuclear localization of p53 and increases the level of transcriptionally active p53 protein. In addition, other studies have found that increased PERP expression affects several aspects of p53 regulation, including increased protein stability, posttranslational modifications, and enhanced nuclear accumulation. These observations place PERP at a critical signaling circuit by influencing pathways of p53 activation, and underscore a unique role for this protein in enhancing functional p53 levels and in increasing p53 stability. A loss of PERP expression promotes tumorigenesis (15). Since SipA promotes the production of PERP the inventors can exploit this natural response as a means to enhance p53 (apoptotic) activity. p53-based drugs have been shown to modify a variety of survival metrics resulting in inhibition of cell proliferation, selective apoptosis in tumor cells, and complete tumor growth inhibition.

In one embodiment, the diseases that are amenable to therapy using any one of the inventions methods include, without limitations, cancer, neuroinflammation (such as multiple sclerosis) (Kooij, G et al., PLoS One. 2009; 4(12): e8212), autoimmune disease (Van de Ven, R. et al., J Leukoc Biol. 2009 November; 86(5):1075-87), and infection with Human Immunodeficiency Virus (HIV) (Jones, K. et al., AIDS. 2001 Jul. 27; 15(10:1353-8).

In a particular embodiment, the invention provides a method for reducing one or more symptoms of cancer in a mammalian subject in need thereof comprising administering to the subject a composition comprising SipA, and/or polypeptide sequence having at least 95% identity to SipA (SEQ ID NO:01). Data herein in Example 6 show that SipA conjugated to gold nanoparticles (SipA-AuNP) improved doxorubicin efficacy in the exemplary murine colon cancer animal model.

In one embodiment, SipA and/or the polypeptide sequence having at least 95% identity to SipA is purified.

The invention's methods are advantageously applicable to cancers that contain cancer cells resistant to at least one cytotoxin.

In one embodiment, the cancer comprises cancer cells that overexpress P-gp and/or p53 compared to a control cell.

In one preferred embodiment, the cancer cells overexpress P-gp. This is exemplified by colorectal cancer (Hota, T. et al., Hepatogastroenterology. 1999 January-February; 46(25):316-21), breast cancer (Bruce, J. et al., JNCI J Natl Cancer Inst (1997) 89 (13): 917-93), bladder cancer (Tada, Y. et al., Int J Cancer. 2002 Apr. 1; 98(4):630-5), sarcomas (including osteosarcoma) (Chan, H S. Et al., J Natl Cancer Inst. 1997 Nov. 19; 89(22):1706-15), astrocytoma (blood brain barrier) (Sadanand et al., Cancer Lett. 2003 Jul. 30; 198(1):21-7), hematological malignancies such as acute myelogenous leukemia (AML) (Leith, C P. et al., Blood. 1999 Aug. 1; 94(3):1086-99) and diffuse large B-cell lymphoma (Yagi, K. et al., Histopathology. 2013 February; 62(3):414-20).

In another preferred embodiment, the cancer cells contain a TP53 mutations. TP53 is the most frequently altered gene in human cancers, it is inactivated in about 50% of human cancers (T. Soussi, C. Béroud, Assessing TP53 status in human tumors to evaluate clinical outcome, Nat. Rev. Cancer, 1 (2001), pp. 233-240).

The invention's compositions are preferably administered in a therapeutic amount. The terms "therapeutic amount," "pharmaceutically effective amount," "therapeutically effective amount," "biologically effective amount," and "protective amount" are used interchangeably herein to refer to an amount that is sufficient to achieve a desired result, whether quantitative and/or qualitative. In particular, a therapeutic amount is that amount that delays, reduces, palliates, ameliorates, stabilizes, prevents and/or reverses one or more symptoms of the disease compared to in the absence of the composition of interest. Examples include, without limitation, tumor size and/or tumor number in cancer disease.

For example, specific "dosages" of a "therapeutic amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors, which those skilled in the art will recognize. The dosage amount and frequency are selected to create an effective level of the compound without substantially harmful effects.

The dosage is adjusted depending on the type and severity of the disease, and, for example, whether there are one or more separate administrations, or continuous infusion. For repeated administrations over several days or longer, depending on the condition, the treatment is repeated until a desired suppression of disease symptoms occurs.

The invention's compositions may be administered prophylactically (i.e., before the observation of disease symptoms) and/or therapeutically (i.e., after the observation of disease symptoms). The term "administering" to a subject means providing a molecule to a subject. This may be done using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789). Administration may be concomitant with (i.e., at the same time as, or during) manifestation of one or more disease symptoms. Also, the invention's compositions may be administered before, concomitantly with, and/or after administration of another type of drug or therapeutic procedure (e.g., surgery). Methods of administering the invention's compositions include, without limitation, administration in parenteral, oral, intraperitoneal, intranasal, topical and sublingual forms. Parenteral routes of administration include, for example, subcutaneous, intravenous, intramuscular, intrasternal injection, and infusion routes. In a particular embodiment, administration is intraperitoneal (see Example 6).

In some embodiments, the invention's compositions may comprise lipids for delivery as liposomes. Methods for generating such compositions are known in the art (Borghouts et al. (2005). J Pept Sci 11, 713-726; Chang et al. (2009) PLoS One 4, e4171; Faisal et al. (2009) Vaccine 27, 6537-6545; Huwyler et al. (2008) Int J Nanomedicine 3, 21-29;

Song et al. (2008) Int J Pharm 363, 155-161; Voinea et al. J Cell Mol Med 6, 465-474), US 2011/0129526 A1.

In one embodiment, the invention's compositions may comprise nanoparticles, microspheres, microparticles, and microcapsules for delivery, using methods known in the art (US 2011/0129526 A1). In on preferred embodiment, the invention's compositions may comprise nanoparticles.

The invention's methods may further comprise administering to the subject one or more cytotoxin. Data herein in Example 6 show a surprising synergistic effect between the cytotoxin doxorubicin and SipA-AuNP, since P-gp expression levels in tumors that received only the SipA-AuNP treatment were modestly reduced (about 10%), wherein the combination of cytotoxin doxorubicin and SipA-AuNP resulted in a significant reduction in p-gp expression levels in tumors (about 40%).

The cytotoxin may be administered before and/or concomitantly with and/or after administration of SipA. Example 6 shows that SipA conjugated to gold nanoparticles improved doxorubicin efficacy in a murine colon cancer animal model.

In some embodiments, SipA is administered in a therapeutic amount that is effective in one or more of a) reducing the level of expression of P-gp in cells of the cancer, b) reducing the level of functional un-cleaved P-gp in cells of the cancer, and c) increasing the level of expression of PERP in cells of the cancer.

For example, SipA may be administered in a therapeutic amount that is effective in reducing the level of expression of P-gp in cells of the cancer (see Examples 2 and 3).

Also, SipA may be administered in a therapeutic amount that is effective in reducing the level of functional un-cleaved P-gp in cells of the cancer. Thus, Example 4 shows that SipA reduces the level of functional P-gp by increasing the level of cleavage of P-gp by caspase-3 (CASP3), thus increasing the level of P-gp cleavage products that comprise the approximately 90 kDa P-gp cleavage product and/or the approximately 60 kDa P-gp cleavage product.

In some embodiments, reducing the level of expression of P-gp comprises a reduction of from 10% to 100% in the mammalian cell compared to in the absence of administering SipA. A reduction of from 10% to 100% includes, for example, a reduction of 10%, 15%, 20%, 25%, 30%, 35%, 40%, 45%, 50%, 55%, 60%, 65%, 70%, 75%, 80%, 85%, 90%, 95%, and 100%. Data herein in Example 3 demonstrate a reduction of P-gp expression by 40% and 95% in breast cancer cells and bladder cancer cells, respectively, following administration of purified SipA.

In some embodiments, the methods further comprise determining the level of expression of P-gp in the mammalian cell, using exemplary methods described in Examples 2 and 3. In some embodiments, the method further comprises determining the level of functional un-cleaved P-gp in the mammalian cell. This may include, for example, determining the level of one or more portions of P-gp, including a P-gp fragment that is produced by cleavage of P-gp with caspase-3. In some embodiments, the P-gp fragment comprises one or more of an approximately 90 kDa P-gp cleavage product and an approximately 60 kDa P-gp cleavage product. Data herein in Example 4 show that SipA reduces the level of functional P-gp by increasing the level of cleavage of P-gp by caspase-3 (CASP3), thus increasing the level of P-gp cleavage products that comprise the approximately 90 kDa P-gp cleavage product and/or the approximately 60 kDa P-gp cleavage product.

In another embodiment, the methods further comprises determining the level of expression of PERP in the mammalian cell.

In particularly preferred embodiments, SipA is operably conjugated to a cytotoxin (e.g., doxorubicin).

In a further embodiment, SipA is operably conjugated to a targeting agent that specifically binds to the cell. As used herein, the term "targeting agent" refers to a chemical moiety that, when associated with (i.e., covalently coupled or otherwise stably associated with) another moiety (such as a therapeutic molecule) in a complex, directs the complex to a specific site where the complex can then be imaged and/or where the complex delivers its associated therapeutic molecule. Suitable targeting agents are known in the art. Representative targeting agents are one of a binding pair. For example, in one embodiment, the targeting agent is an antibody, an antigen-binding portion of the antibody, or its antigen. The antigen can be a small molecule, peptide, protein, polynucleotide, or polysaccharide. In one embodiment, the targeting agent is a nucleic acid or its complement. The nucleic acids can be DNAs and RNAs. In one embodiment, the targeting agent is an enzyme or its substrate. In one embodiment, the targeting agent is a receptor or its ligand. In one embodiment, the targeting agent is a nucleic acid or its partner protein. In one embodiment, the targeting agent is a ligand for a cell, a cell membrane, or an organelle.

In one embodiment, targeting agents that specifically binds to a cancer cell include folic acid, and "cyclic-arginine-glycine-aspartic acid" ("cRGD") peptide. RGD-4C-Peptide has been shown to specifically bind to human breast cancer cells as well as to cancer endothelial cells, in vivo (Zitsmann et al. Cancer Res Sep. 15, 2002 62; 5139).

Antibodies that specifically bind to cancer cells are known in the art including those specific for breast cancer (US 2004/0151724), prostate-specific membrane antigen (PSMA) antibody specific for prostate cancer (WO 2011/057146), EGFR antibody specific for glioblastoma (WO 2011/057146), AFAI antibody specific for lung cancer (US 2009/0226942 and US 2006/0159687 and WO 2004/078097), urinary tumor associated antigen (UTAA) specific antibodies such as TA90 specific antibodies (U.S. Pat. Nos. 5,700,649 and 5,993,828, US 2010/0247440).

In certain embodiments, such as imaging or treating tumors, antibodies of use may target tumor-associated antigens. These antigenic markers may be substances produced by a tumor or may be substances which accumulate at a tumor site, on tumor cell surfaces or within tumor cells. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744. Reports on tumor associated antigens (TAAs) include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63).

Another marker of interest is transmembrane activator and CAML-interactor (TACI). See Yu et al. Nat. Immunol. 1:252-256 (2000).

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, B7, MUC1, Ia, Ii, HM1.24, HLA-DR, tenascin, VEGF, PlGF, ED-B fibronectin, an oncogene (e.g., c-met or PLAGL2), an oncogene product, CD66a-d, necrosis antigens, IL-2, T101, TAG, IL-6, MIF, TRAIL-R1 (DR4) and TRAIL-R2 (DR5).

In a particularly preferred embodiment, the targeting agent is exemplified by an antibody, an antigen-binding portion of an antibody, cyclic-arginine-glycine-aspartic acid (cRGD) peptide, and folic acid.

The invention further provides a method comprising administering to a mammalian cell a composition comprising SipA, and/or polypeptide sequence having at least 95% identity to SipA (SEQ ID NO:01), wherein SipA (and/or the polypeptide sequence) is in an amount that is effective in one or more of a) reducing the level of expression of P-gp in the cell (see Examples 2 and 3), b) reducing the level of functional un-cleaved P-gp in the cell (see Example 4, which shows that SipA reduces the level of functional P-gp by increasing the level of cleavage of P-gp by caspase-3 (CASP3), thus increasing the level of P-gp cleavage products that comprise the approximately 90 kDa P-gp cleavage product and/or the approximately 60 kDa P-gp cleavage product), and c) increasing the level of expression of PERP in the cell.

In one embodiment, SipA and/or the polypeptide sequence having at least 95% identity to SipA is purified.

In some embodiments of the inventions' methods, the cell overexpresses one or more of P-gp and p53 compared to a control cell.

In particularly preferred embodiments, the cell that overexpresses p53 is a cancer cell.

In another particularly preferred embodiment, the cell that overexpresses P-gp is a cancer cell and/or a non-cancerous cell.

In some embodiments, the cell is in vitro and/or in vivo.

Exemplary non-cancerous cells that overexpress P-gp comprise a lymphocyte cell, such as a lymphocyte infected with HIV.

In another embodiment, non-cancerous cells that overexpress P-gp comprise an intestinal epithelial cell. Data herein in Example 6 demonstrate that SipA significantly deceased expression of P-gp in mice that were infected with a *Salmonella typhimurium* strain that overexpressed SipA, compared to an isogenic *S. typhimurium* mutant strain.

In some embodiments, the cancer cell that overexpresses P-gp comprises one or more of a colon cancer cell (see Example 2), colorectal cancer cell, gastro-intestinal cancer cell, breast cancer cell (see Example 3), bladder cancer cell (see Example 3), kidney cancer cell, leukemia cell, brain cancer cell, sarcoma cell, astrocytoma cell, acute myelogenous leukemia (AML) cell, and diffuse large B-cell lymphoma cell.

In some embodiments, the cancer cell is in vivo, and SipA administration may be oral, transdermal, intravenous, intraperitoneal (see Example 6), and/or by local injection.

In alternative embodiments, the cancer cell is in vivo, and SipA administration is before and/or concomitantly with and/or after administration of a cytotoxin.

4. SipA Conjugated to Nanoparticles

The invention further provides a nanoparticle comprising one or more purified SipA and/or one or more polypeptide sequence having at least 95% identity to SipA (SEQ ID NO:01).

The functional design of the invention's nanocarrier particles was founded on the inventors' discovery that the *Salmonella* effector protein, SipA targets two pathways critical for improving chemotherapeutic efficacy: multidrug resistance and stabilizing p53, a tumor suppressor protein. The innovation of this technology and the unconventional nature of the approach was centered on the development of a novel AuNP (gold nanoparticle) scaffold in which SipA was engineered as part of a drug nanocarrier that works in combination with a known chemotherapeutic drug, such as doxorubicin. In essence the inventors created a nanoparticle that acts as a bacterial mimic to reduce (including reverse) multidrug resistance.

The invention's methods that employ SipA conjugated to nanoparticles (such as the SipA-conjugated AuNP bacterial mimic) capitalize on the unique chemical and physical properties of AuNPs, the biochemical functional activities of SipA, and can be used as a stand-alone treatment, and/or in conjunction with many different FDA approved chemotherapeutic agent, such as doxorubicin. If desired, the SipA-AuNP system can additionally be conjugated with an acceptor molecule that recognizes its cognate receptor on the surface of target tumor cells; e.g., antibodies, cyclic-arginine-glycine-aspartic acid (cRGD) peptide and folic acid. Such conjugation further improves the tumor targeting capabilities of the SipA-AuNP system to minimize unwanted off-target p-gp effects. In sum, such bacterial mimics present a facile and powerful system to overcome multidrug resistance in tumor chemotherapy that can be combined with different anti-cancer drugs to target a variety of cancers, including colon, breast, and leukemia.

The invention's compositions are useful in any one of the invention's methods. In a particular embodiment, SipA is operably conjugated to a nanoparticle. In another embodiment, the nanoparticle is further operably conjugated to a cytotoxin and/or targeting agent that specifically binds to a cell. In some embodiments, the targeting agent that specifically binds to the cell comprises one or more of antibody, antigen-binding portion of an antibody, cyclic-arginine-glycine-aspartic acid peptide (cRGD).

In some embodiment, the nanoparticle comprises a gold nanoparticle, such as a nanoparticle from 1 nm to 100 nm. In a particularly preferred embodiment, the nanoparticle is 15 nm. Data herein in Example 5 describe the construction and use of exemplary 15 nm gold nanoparticles conjugated to SipA via tetra ethylene glycol (TEG) surface ligand spacers.

Figure 5:
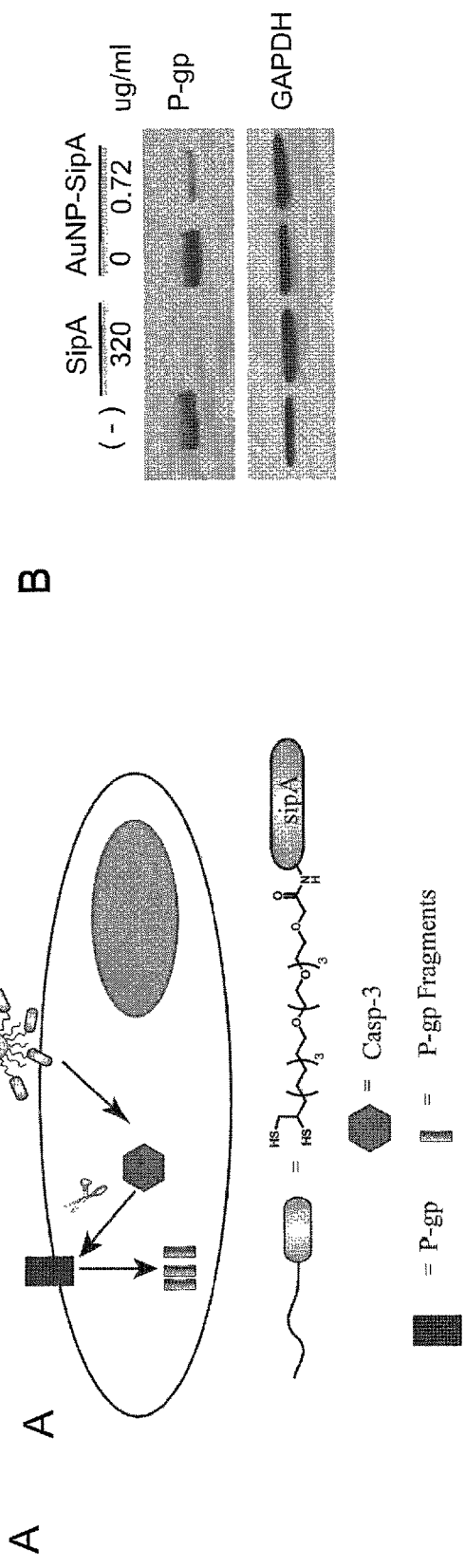
FIG. 5. SipA-AuNPs decrease the expression of P-gp at a SipA dose nearly 500 times lower than free SipA. (A) Schematic presentation of P-gp knockdown mechanism via SipA-AuNP. (B) HCT8 cell monolayers were left untreated (-), exposed to 320 µg/ml 160 µg/ml of purified SipA, AuNP alone or AuNP-SipA (0.72 µg/ml of SipA).

In some embodiments, SipA is operably conjugated at a nanoparticle:SipA ratio of at least 1:1. In one embodiment, the nanoparticle:SipA ratio is any ratio from 1:1 to 1:100 including from 1:5, from 1:2, from 1:3, from 1:4, from 1:5, from 1:6, from 1:7, from 1:8, from 1:9, from 1:10, from 1:11, from 1:12, from 1:13, from 1:14, from 1:15, from 1:16, from 1:17, from 1:18, from 1:19, from 1:20, etc. In a preferred embodiment, the nanoparticle:SipA ratio is 1:6. Data herein in Example 5 demonstrate the successful construction of SipA conjugated to gold particles at a nanoparticle:SipA ratio of 1:6, and the successful use of these particles to reduce the level of P-gp expression in cancer cells at SipA doses that are nearly 500 times lower than in free unbound SipA (FIG. 5B).

In some embodiments, the invention's compositions comprise any one or more of the nanoparticles described herein and at least one pharmaceutically acceptable molecule, such as diluent and/or excipient.

Exemplary "diluent" ("carrier") includes water, saline solution, human serum albumin, oils, polyethylene glycols, aqueous dextrose, glycerin, propylene glycol or other synthetic solvents. Diluents may be liquid (such as water, saline, culture medium, saline, aqueous dextrose, and glycols) or solid carriers (such as carbohydrates exemplified by starch, glucose, lactose, sucrose, and dextrans, anti-oxidants exemplified by ascorbic acid and glutathione, and hydrolyzed proteins).

An "excipient" is an inactive substance used as a carrier for the invention's compositions that may be useful for delivery, absorption, bulking up to allow for convenient and accurate dosage of the invention's compositions. Excipients include, without limitation, antiadherents, binders (e.g., starches, sugars, cellulose, modified cellulose such as hydroxyethyl cellulose, hydroxypropyl cellulose and methyl cellulose, lactose, sugar alcohols such as xylitol, sorbitol and maltitol, gelatin, polyvinyl pyrrolidone, polyethylene glycol), coatings (e.g., shellac, corn protein zein, polysaccharides), disintegrants (e.g., starch, cellulose, crosslinked polyvinyl pyrrolidone, sodium starch glycolate, sodium carboxymethyl cellulose), fillers (e.g., cellulose, gelatin, calcium phosphate, vegetable fats and oils, and sugars, such as lactose), diluents, flavors, colors, glidants (e.g., silicon dioxide, talc), lubricants (e.g., talc, silica, fats, stearin, magnesium strearate, stearic acid), preservatives (e.g., antioxidants such as vitamins A, E, C, selenium, cystein, methionine, citric acids, sodium citrate, methyl paraben, propyl paraben), sorbents, sweeteners (e.g., syrup). In one embodiment, the excipient comprises HEC (hydroxyethylcellulose), which is a nonionic, water-soluble polymer that can thicken, suspend, bind, emulsify, form films, stabilize, disperse, retain water, and provide protective colloid action. HEC is non-inflammatory and has been used as a delivery vehicle for vaginal microbiocides (Tien et al., AIDS Research & Human Retroviruses, (2005). 21:845).

EXPERIMENTAL

The following examples serve to illustrate certain preferred embodiments and aspects of the present invention and are not to be construed as limiting the scope thereof.

Example 1

Materials and Methods

The following is a brief description of the exemplary materials and methods used in the subsequent Examples.

Chemicals.

Anti-P-gp mouse mAb C219 and C494 were purchased from CalBiochem (La Jolla, Calif.). The CASP3 inhibitor (SC-3075) and CASP1 inhibitor (SC-3071) were purchased from Santa Cruz Biotechnology (Santa Cruz, Calif.). The Anti-HA affinity matrix and HA peptide were purchased from Roche applied science (Mannhein, Germany).

Cell Culture.

The human intestinal adenocarcinoma cell line HCT8 were maintained in accordance with (8). The human breast adenocarcinoma cell line MCF-7, the human bladder transitional cell carcinoma cell line UM-UC-3, and the CT26 murine colon carcinoma cell line, were purchased from ATCC and were all maintained in DMEM F-12 containing a 10% fetal bovine serum, 100 U/ml penicillin, and 10 µg/ml streptomycin at 37° C. in 90% relative humidity and 5% $CO_2$.

Bacterial Strains, Plasmids and Growth Conditions.

All S. Typhimurium strains are derived from SL1344. The AKJ63 strain has been previously described (22). Additionally, ΔSipC, ΔSipB, and ΔSopA have all been previously described (9, 11).

Isolation of S. Typhimurium Secreted Proteins.

Wild type S. Typhimurium SL1344 or mutants were grown in LB medium overnight in accordance with (22). The proteins from the culture supernatants were precipitated with 10% (vol/vol) trichloroacetic acid, as previously described (9).

The Purification of SipA-HA Fusions Protein.

The purification of SipA was preformed in accordance with the work of Lee et al, (22).

Cell Lysates and Western Blot Analysis.

Cell lysates were harvested from S. Typhimurium-infected HCT8 cells, as previously described (8). Proteins were normalized to 30 µg, separated by SDS/PAGE (4-12% gradient; Biorad, Hercules, Calif.), and transferred to nitrocellulose (Bio-Rad; 0.45µ membrane) Immuno-blots were performed using the murine monoclonal P-gp C219 antibody (calbiochem) diluted at 1:100. A goat anti-mouse IgG labeled with horseradish peroxidase (Santa Cruz, Calif.) diluted at 1:10000 was used to detect the bands, which were visualized by enhanced chemiluminescence using a super signal West pico kit (Theinio, Rockford, Ill.).

SipA-AuNP Conjugation Chemistry:

1. A Synthesis of the Dithiolated Tetra (Ethylene Glycol) Carboxylic Acid.

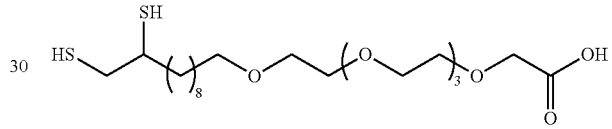

A synthesis of Undec-1-en-11-yltetra (ethylene glycol). A mixture of 0.34 mL of 50% aqueous sodium hydroxide (4.3 mmol) and 4.08 g of tetra (ethylene glycol) (21 mmol) was stirred for about 0.5 h in an oil bath at 100° C. under an atmosphere of argon, and then 1.0 g of 11-bromoundec-1-ene (4.3 mmol) was added. After 24 h, the reaction mixture was cooled and extracted six times with hexane. Concentration of the combined hexane portions by rotary evaporation at reduced pressure gave yellow oil containing a mixture of mono- and diethers, according to analysis by $^1$HNMR spectroscopy. Purification of the oil by chromatography on silica gel (eluant: ethyl acetate) gave 0.98 g of monoether: 76% yield; $^1$H NMR (400 MHz, CDCl,) 1.22-1.27 (m, 10H), 1.29-1.34 (m, 2H), 1.49-1.56 (m, 2H), 1.96-2.02 (m, 2H), 2.73-2.76 (t, 1H), 3.38-3.42 (t, 2H, J=7 Hz), 3.52-3.69 (m, 16H), 4.86-4.97 (m, 2H), 5.71-5.82 (m, 1H). MS (ESI-MS) calcd for $C_{19}H_{38}O_5$ 346.50, found 347.2 $[M+H]^+$.

To a solution of Undec-1-en-11-yltetra(ethylene glycol) (1.0 g 2.89 mmol) in dry DCM (6 mL) at 0° C. was added ethyl diazoacetate (0.7 mL, 5.78 mmol) and $BF_3Et_2O$ (0.29 mmol). After the mixture was stirred for 30 min at 0° C., saturated ammonium chloride (3 mL) was added and the reaction mixture was placed in a separated funnel. The organic phase was collected and the aqueous phase was extracted with DCM (5*150 mL). The combined organic phase was dried over $Na_2SO_4$ and concentrated to a yellow oil, which was purified by chromatography using gradient elution hexane (1:1) to ethyl acetate to offered ester. $^1$H NMR (400 MHz, CDCl,) 1.19-1.22 (m, 13H), 1.26-1.31 (m, 2H), 1.46-1.52 (m, 2H), 1.93-1.98 (m, 2H), 3.35-3.38 (t, 2H, J=7 Hz), 3.52-3.69 (m, 16H), 4.11-4.16 (m, 2H), 4.07 (s, 2H), 4.82-4.93 (m, 2H), 5.69-5.77 (m, 1H). MS (ESI-MS) calcd for $C_{23}H_{44}O_7$ 432.31, found 450.2 $[M+H_3O]^+$.

To a solution of ester (0.10 g, 0.23 mmol) in dry DCM (10 mL) was added bromine (0.28 mmol) at 0° C. The reaction mixture was stirred at 0° C. for 4 hours at the dark. Thereafter, the reaction mixture was isolated by removal of the solvent using a slight vacuum and a water bath temperature of 30° C. in a rotary evaporator and final drying of the product in vacuum. $^1$H NMR (400 MHz, CDCl,) 1.22-1.38 (m, 13H), 1.49-1.61 (m, 4H), 1.71-1.80 (m, 2H), 3.42-3.47 (t, 2H, J=7 Hz), 3.58-3.77 (m, 17H), 3.81-4.87 (m, 1H), 4.17 (s, 2H), 4.19-4.22 (m, 3H). MS (ESI-MS) calcd for $C_{23}H_{44}Br_2O_7$ 592.40, found 615.2 $[M+Na]^+$.

A solution of dibromine (100 mg, 0.17 mmol) and $K_2CO_3$ (117 mg, 0.85 mmol) in acetone (10 mL) was added thioacetic acid (129 mg, 1.7 mmol). The reaction mixture was stirred at room temperature overnight. $^1$H NMR (400 MHz, CDCl,) 1.09-1.35 (m, 13H), 1.48-1.68 (m, 4H), 1.93-2.01 (m, 2H), 2.32 (s, 6H), 3.08-3.28 (m, 1H), 3.39-3.50 (m, 3H), 3.55-3.78 (m, 17H), 4.15 (s, 2H), 4.18-4.24 (m, 2H). MS (ESI-MS) calcd for $C_{27}H_{50}O_9S_2$ 582.81, found 621.3 $[M+K]^+$.

The solution of diactyl-OEt in ethyl was then added concentrated hydrochloric acid and stirred overnight to provide free thiol compound. $^1$H NMR (400 MHz, CDCl,) 1.18-1.38 (m, 10H), 1.49-1.61 (m, 8H), 2.72-2.98 (m, 3H), 3.36-3.42 (t, 2H, J=7 Hz), 3.55-3.77 (m, 16H), 4.17 (s, 2H). MS (ESI-MS) calcd for $C_{21}H_{42}O_7S_2$ 470.68, found 471.3 $[M+H]^+$.

2. Syntheses of the Au—COOH.

15 nm of AuNPs were first synthesized using citrate as a reducing agent and stabilizer. HAuCl4 (10 mg) was dissolved in 90 ml of water, and the solution was heated to the boiling point. Sodium citrate solution (500 µl of 250 mM) was added to the boiling solution and stirred for 30 minutes until the color turned to wine-red. The resulting AuNP was then washed three times. Five mg of the dithiolated tetra (ethylene glycol) carboxylic acid was subsequently mixed with 10 pmoles of AuNPs in 5 ml of water, leading to an overnight ligand change reaction. The afforded Au—COOH nanoparticles were dialyzed in DI water using a Slide-A-Lyzer MINI dialysis unit (MW=10,000) for two days.

3. Conjugation and Characterization of the SipA Conjugated AuNPs.

1-Ethyl-3-(3-dimethylaminopropyl)carbodiimide (EDC) 10 mg and N-hydroxysuccinimide (NHS) 10 mg were added to a 28 ml (7.20 pmols) solution of Au—COOH. The resultant solution was stirred at room temperature. After 1 h, the solution was centrifuged and washed three times with DI water. Finally, the solution was concentrated to 2 ml of DI water. 200 µl (540.7 µg/ml) SipA solution was added to this solution. This mixed solution was stirred in a cold room that was 4° C. After 12 h, the solution was centrifuged and washed three times with DI water. Finally, the SipA-AuNP stock solution was concentrated to 0.5 ml of DI water and was then dialyzed with Slide-A-Lyzer MINI dialysis unit (MW=100,000) in DI water overnight.

The Subcutaneous Tumor Model.

Female 8 to 10 week old Balb/C mice were purchased from Jackson Laboratory (Bar Harbor, Me.) and allowed to acclimatize for 4 days. CT26 cells were harvested by trypsin treatment, washed twice in PBS buffer, and resuspended in PBS. CT26 cells ($5\times10^5$) were inoculated in 100 µl subcutaneously in to the right flank (16). Mice were randomly assigned to the control group (n=6) or the treatment groups (n=6)/group. After several days, the mice harbored tumors with volumes of ~0.5 mm$^3$, and were IP injected with 1.1 µg/day of SipA-AuNP (200 ul) for two days. The following day, the mice received a one-time drug treatment of Doxorubicin (10 mg/kg) delivered by IP injection, followed by 1.1 µg/day of SipA-AuNP (IP) every 48 hours for 15 days. Two weeks post drug delivery the mice were sacrificed and the tumors were extracted for analysis, in regard to tumor size and expression of P-gp. Tumor size was measured using calipers and volumes were estimated using the formula $0.5\times length\times(width)^2$. The care of these animals was in accordance with University of Massachusetts Medical School institutional guidelines under protocol number: 2046-12. Statistical analysis was performed using Prism software (GraphPad).

Mouse Infections.

Mouse infections were performed as previously described (9).

Example 2

SipA Modulates the Expression of P-gp in Intestinal Epithelial Cells

Since the inventors' prior work revealed that *S. Typhimurium* SPI-1 is necessary to down regulate the expression of P-gp (8), the inventors began by screening *S. Typhimurium* type III secreted effectors to determine if any are altered in their ability to modulate P-gp. the inventors found that when HCT8 human intestinal carcinoma cell monolayers were exposed to *Salmonella* mutants of the type III secretion system translocon, ΔSipB or ΔSipC, these mutants maintained the ability to modulate P-gp (FIG. 1A). Phenotypically, these mutants are able to secrete effectors but they fail to translocate them into the host cells (9). the inventors' findings therefore suggest that a secreted effector could be modulating P-gp as a result of an extracellular interaction rather than due to its direct delivery into epithelial cells. To examine this possibility, HCT8 epithelial monolayers were exposed to an extract of secreted proteins that were isolated from *S. Typhimurium* (Example 1). Since the treatment of this protein extract alone is sufficient to trigger the modulation of P-gp (FIG. 1B), the inventors next examined individual *S. Typhimurium* type III secreted effector mutants to establish whether any fail to modulate P-gp. As shown in FIG. 1C, a *S. Typhimurium* ΔSipA mutant strain (EE633) is dramatically reduced in its ability to modulate P-gp. The specificity of the ΔsipA mutant defect was verified by demonstrating that a plasmid that expresses the sipA gene restores the ability of the ΔsipA mutant to modulate P-gp to the approximate levels elicited by the wild-type strain (FIG. 1C).

Figure 2:
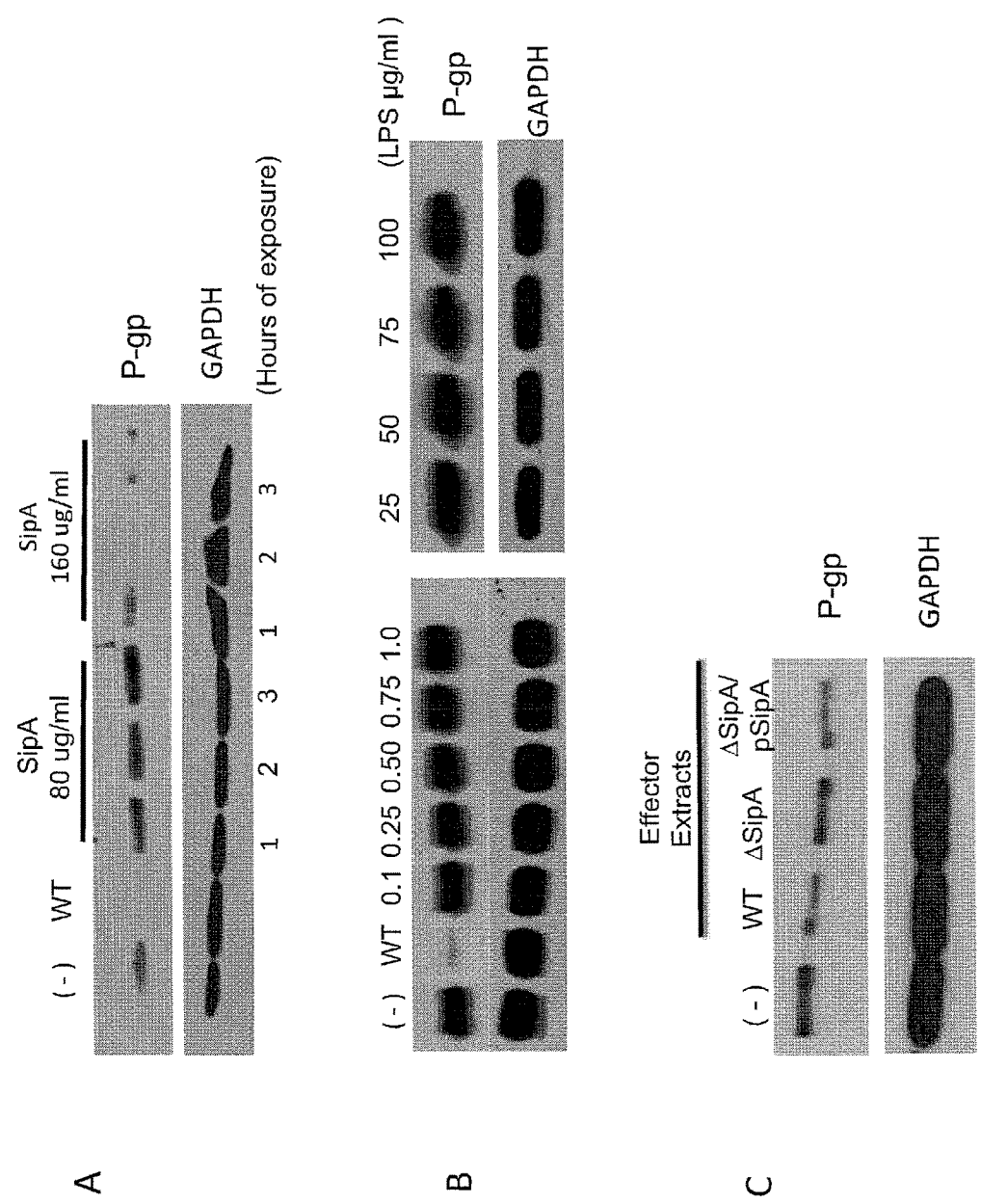
FIG. 2. SipA down-regulates P-gp expression in a dose-dependent manner. (A) HCT-8 cell monolayers were left untreated (-) or infected with wild type SL1344 or exposed to 80 μg/ml or 160 μg/ml of purified SipA over a time course of 3 h. Normalized whole cell lysates were then probed for P-gp and GAPDH. (B) HCT8 cell monolayers were infected with wild type SL1344 or exposed to purified lipopolysaccharide (LPS) from *S. typhimurium* (0.1 to 100 μg/ml) for 3 h, and then probed as in (A). (C) HCT8 cell monolayers were exposed to secreted protein extracts from SL1344 wild type, ΔsipA or ΔSipA/pSipA for 3 h, and then probed as in (A).

To examine whether SipA alone can induce the modulation of P-gp without the assistance of other *Salmonella* or type III effectors, purified SipA-HA was added to buffer overlying washed HCT8 cells. Exposure of cell monolayers to 80 µg/ml or 160 µg/ml of SipA-HA over a period of 3 hours resulted in a dose dependent ability to modulate P-gp to the same degree as wild-type *S. Typhimurium*. This effect was not attributed to trace amounts of lipopolysaccharide (FIGS. 2A and B). Moreover, to further validate that SipA was responsible for the modulation of P-gp, monolayers were exposed to an extract of secreted proteins isolated from the *S. Typhimurium* ΔSipA mutant (Example 1). This extract contained all *S. Typhimurium* secreted effectors with the exception of SipA, and as shown in FIG. 2C, failed to modulate P-gp. Monolayers were also exposed to a secreted protein extract from the regenerated mutant, *S. Typhimurium* ΔSipA/pSipA, which was rescued in its ability to modulate P-gp (FIG. 2C).

Example 3

Figure 3:
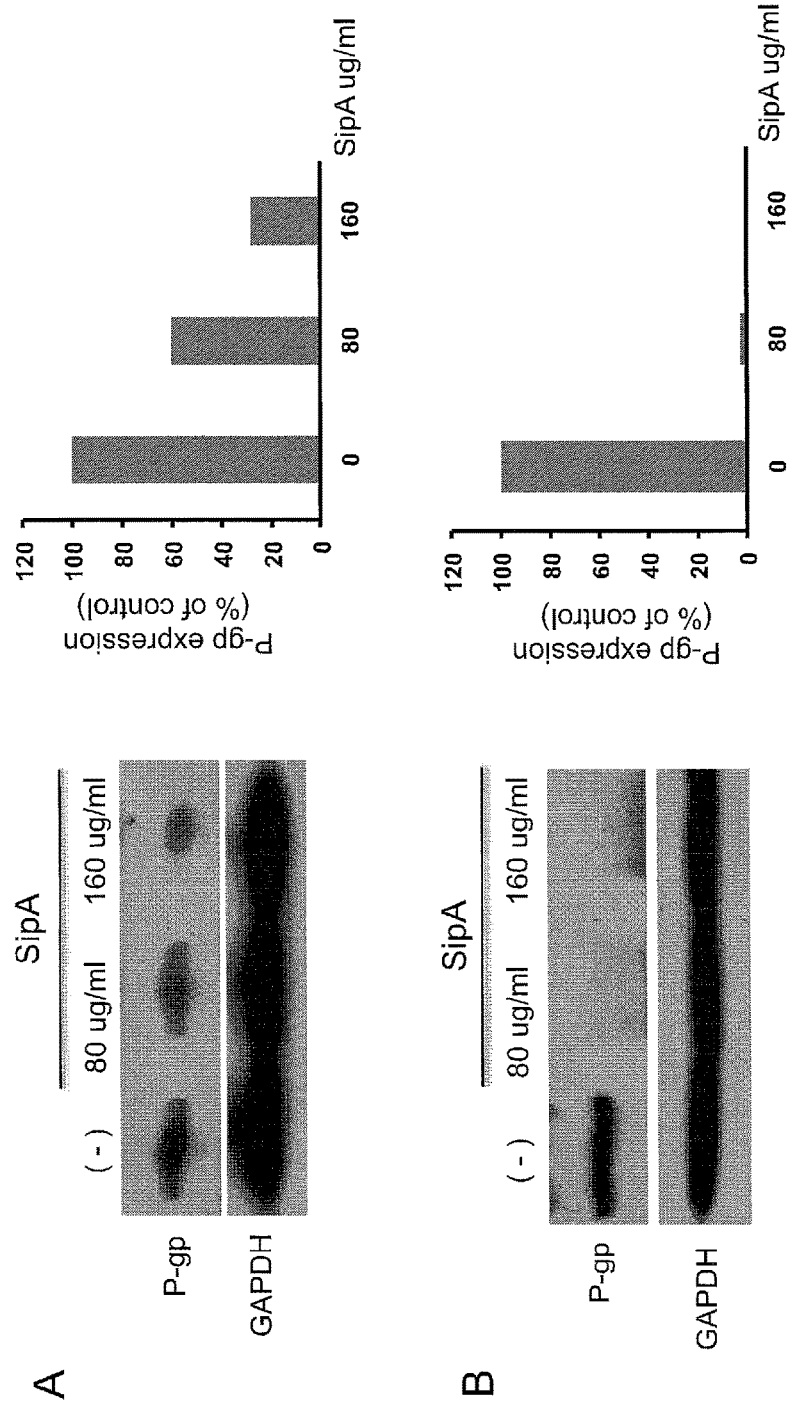
FIG. 3. SipA-induced, dose-dependent P-gp down-regulation is conserved in other cancer cell types. (A) MCF-7 breast adenocarcinoma cells were left untreated (-) or exposed to 80 μg/ml or 160 μg/ml of purified SipA for 3 h. Normalized whole cell lysates were then probed for P-gp and GAPDH. Densitometry was analyzed by ImageJ and presented as relative to the untreated cells. (B) UM-UC-3 human bladder carcinoma cells were left untreated or exposed to 80 μg/ml or 160 μg/ml of purified SipA for 3 h, and then probed and analyzed as in (A).

SipA Modulates the Expression of P-gp in Breast and Bladder Human Cancer Cell Lines Because P-gp expression is documented to be up-regulated in several types of malignancies, and contributes to their poor prognosis (6, 7), the inventors assessed whether the ability of SipA to down-regulate P-gp is broad spectrum. Similar to colonic cancer cell lines, purified SipA-HA was exposed to cell monolayers of different cancer cell types that are also known to over-express P-gp, such as MCF-7 (breast adenocarcinoma), and UM-UC-3 (human bladder carcinoma). Compared to the buffer control, the exposure of purified SipA to MCF-7 cells reduced the expression of P-gp in a dose dependent manner demonstrating a 40% reduction. Likewise, the inventors also found that SipA-HA modulates the expression of P-gp on UM-UC-3 cells, showing a 95% reduction. Exposure of SipA-HA to HCT8 cells served as the positive control (FIGS. 3A and B). These results confirm that the ability of SipA to modulate P-gp is not restricted to intestinal epithelial cells.

Example 4

Mechanism of SipA Action on P-pg

Figure 4:
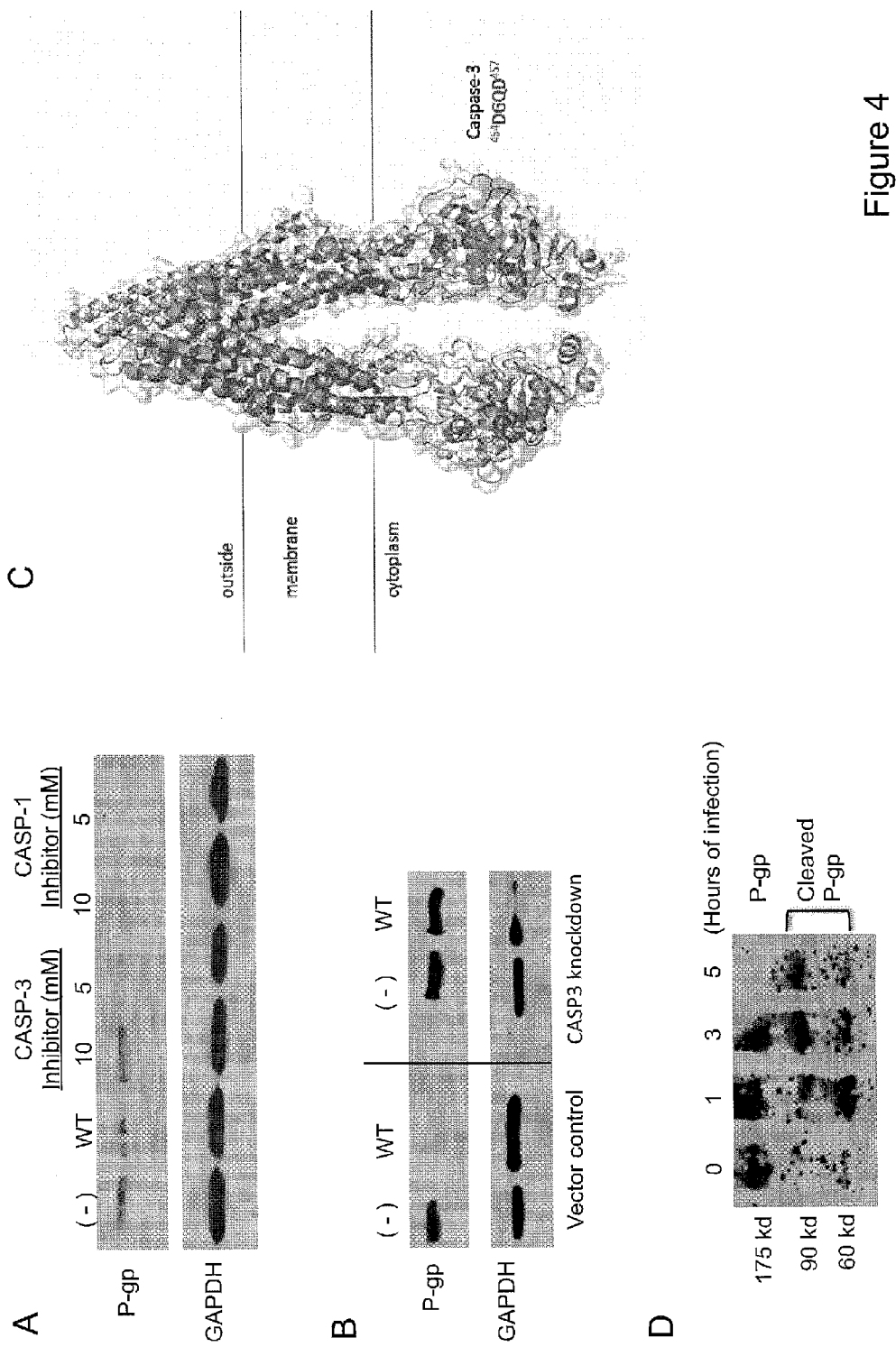
FIG. 4. *S. Typhimurium* modulates P-gp expression through a caspase-3-dependent mechanism. (A) HCT8 cell monolayers were left untreated (-) or infected with wild type SL1344 in the presence or absence of pharmacological inhibitors of CASP-3 or CASP-1 (negative control) for 5 h. Normalized whole cell lysates were then probed for P-gp and GAPDH. (B) HCT8 cell monolayers transfected with a nonspecific siRNA vector control or with siRNA aimed at decreasing CASP-3 expression were left untreated or infected with wild type SL1344. Whole cell lysates were then probed as in (A). (C) Three-dimensional structure of mouse P-gp (PDB ID, 3G5U) depicted as cartoon and transparent surface. The cytoplasmic Caspase-3 cleavage site ($^{454}$DGQD$^{457}$) is shown in red. The putative CASP3 site $^{164}$DVHD$^{167}$ is not shown. Numbers refer to the position of the amino acids in the protein sequence. (D) HCT8 cell monolayers were infected with wild type SL1344 for 1, 3 or 5 h, and then probed using a P-gp antibody capable of detecting P-gp cleavage products. Progressive P-gp modulation was accompanied by the occurrence of 90 and 60 kDs cleavage products.

Our prior studies revealed that protein expression of P-gp is down-regulated in *Salmonella*-infected epithelial cells without a corresponding decrease in P-gp mRNA. This observation is consistent with a mechanism of P-gp protein cleavage and/or rearrangement from the cell membrane rather than the regulation of gene expression. Recent studies using human T-lymphoblastoid CEM cells have shown that P-gp undergoes caspase-3-dependent cleavage during apoptosis (10), providing evidence that cells are able to functionally down-regulate P-gp through a mechanism involving protein cleavage/degradation. Since the inventors have previously shown that the SipA effector protein is necessary and sufficient to promote the activation of caspase-3 (CASP3) (11), the inventors next examined the protein expression of P-gp in HCT8 cells following infection from *S. Typhimurium* in the absence and presence of a pharmacological inhibitor of CASP3. As shown in FIG. 4A, Western blot analysis demonstrates that caspase-3, but not CASP1 inhibition (which was used as the negative control), prevented *S. Typhimurium* from down-regulating P-gp. A similar outcome was also observed using HCT8 cells knocked-down (small interfering RNA (siRNA;(11))) for the expression of CASP3 (FIG. 4B), further supporting the contention that P-gp undergoes CASP3-dependent cleavage as a means to functionally down-regulate this transporter. Moreover, in silico modeling of mouse P-gp (which is 89% identical to the human P-gp) revealed two surface-exposed CASP3 cleavage motifs (DQGD and DVHD; FIG. 4C). In line with this observation, the inventors also found that HCT-8 cells infected with *S. Typhimurium* showed a progressive reduction in the expression of P-gp, and this correlated with the appearance of the predicted CASP3 cleavage products of P-gp (90 kDa, and approximately 60 kDa), as calculated from the in silico model (FIGS. 4C and D). The lower 25 kDa band was not resolved. Taken together, these observations suggest that the ability of *S. Typhimurium* to modulate P-gp via SipA depends on its ability to activate CASP3, and is consistent with the inventors' previous findings showing that SipA activates CASP3.

Example 5

Construction of SipA-AuNP

Capitalizing on the ability of SipA to broadly down-regulate P-gp, the inventors next sought to engineer SipA conjugated nanoparticles as an effective chemotherapeutic adjuvant. the inventors selected gold nanoparticles as a scaffold because these particles are inert/not toxic,(12, 13) easily synthesized and modified, and stabilize conjugated pharmaceutics (e.g., proteins(14) and small molecule drugs (12)). The inventors fabricated 15 nm gold nanoparticles for this work since nanoparticles that are less than 100 nm have a unique enhanced permeation and retention (EPR) effect, and can, therefore effectively extravasate and remain within interstitial spaces, resulting in a much higher concentration of SipA at tumor sites(15).

Although substantial progress has been made in promoting the use of AuNPs for genetic material and as small molecular drug delivery systems, the delivery of functional proteins with retention or enhanced activity has been challenging due to inadequate maintenance of protein recognition and structure retention. To overcome this limitation, the inventors designed surface ligands for direct conjugation of SipA to the AuNP by inserting biocompatible tetra (ethylene glycol) (TEG) spacers (Example 1 and FIG. 5A). This adaptation reduces non-specific interactions and absorption, and provides additional degrees of freedom and polyvalency for enhancing the conjugated protein's activity. Moreover, the carboxylate terminus creates a platform for subsequent protein coupling. Lastly, the inventors covalently attached the SipA proteins to the carboxyl modified AuNP in order to avert protein dissociation or aggregation (Example 1 and FIG. 5A).

To determine the ratio of AuNP to surface conjugated SipA proteins, the inventors next exposed the SipA-AuNP to sodium cyanide, which decomposes the gold particle core. This mixture was then dialyzed for two days using a Slide-A-Lyzer MINI dialysis unit (MW=10,000), and thereafter concentrated to 45 µl for mass spectrometry characterization. Based on mass spectrometry analysis, the total amount of SipA protein was determined to be 42.2 pmols, establishing the binding ratio of AuNP:SipA at 1:6 (Example 7). Subsequent in vitro testing of the SipA-conjugated AuNP revealed that the design of this novel nanoparticle profoundly increases the stability of surface bound SipA protein and reduces P-gp expression in cancer cells at SipA doses that are nearly 500 times lower than in free unbound SipA (FIG. 5B). Such enhanced SipA functionality is most likely due to the large surface (the volume ratio of AuNP), which dramatically stabilizes SipA proteins by preventing the conjugated proteins from degradation. Additionally, the polyvalency of SipA proteins on the surface of single AuNP may offer a synergistic cooperation effect, which does not exist in free-bound SipA.

Example 6

SipA-AuNP Improves the Efficacy of Doxorubicin in a Murine Colon Cancer Model We next sought to determine whether the SipA-AuNP conjugate improves the efficacy of doxorubicin, a known chemotherapeutic drug the inventors used a well-established subcutaneous murine colon cancer model as a prototypical model to study cancers that are known to overexpress P-gp (16) (17). Disease in this model is induced by the subcutaneous injection of CT26 colon cancer cells in ~8 week old Balb/C mice. The formation of palpable tumors (approximately 0.5 mm$^3$ in size) denotes day 1 of the experiment. Mice were then IP injected with 1.1 µg/day of SipA-AuNP for two days prior to IF treatment of a single dose of doxorubicin (10 mg/kg). Since the key objective is to assess whether SipA-AuNP itself is able to improve doxorubicin efficacy, 10 mg/kg identifies a concentration of the drug that the inventors determined displays a minimal effect on tumor size. This treatment was followed by SipA-AuNP IP injections every 48 hours for 15 days, after which, doxorubicin efficacy was assessed by the tumor volume in mm$^3$.

Figure 6:
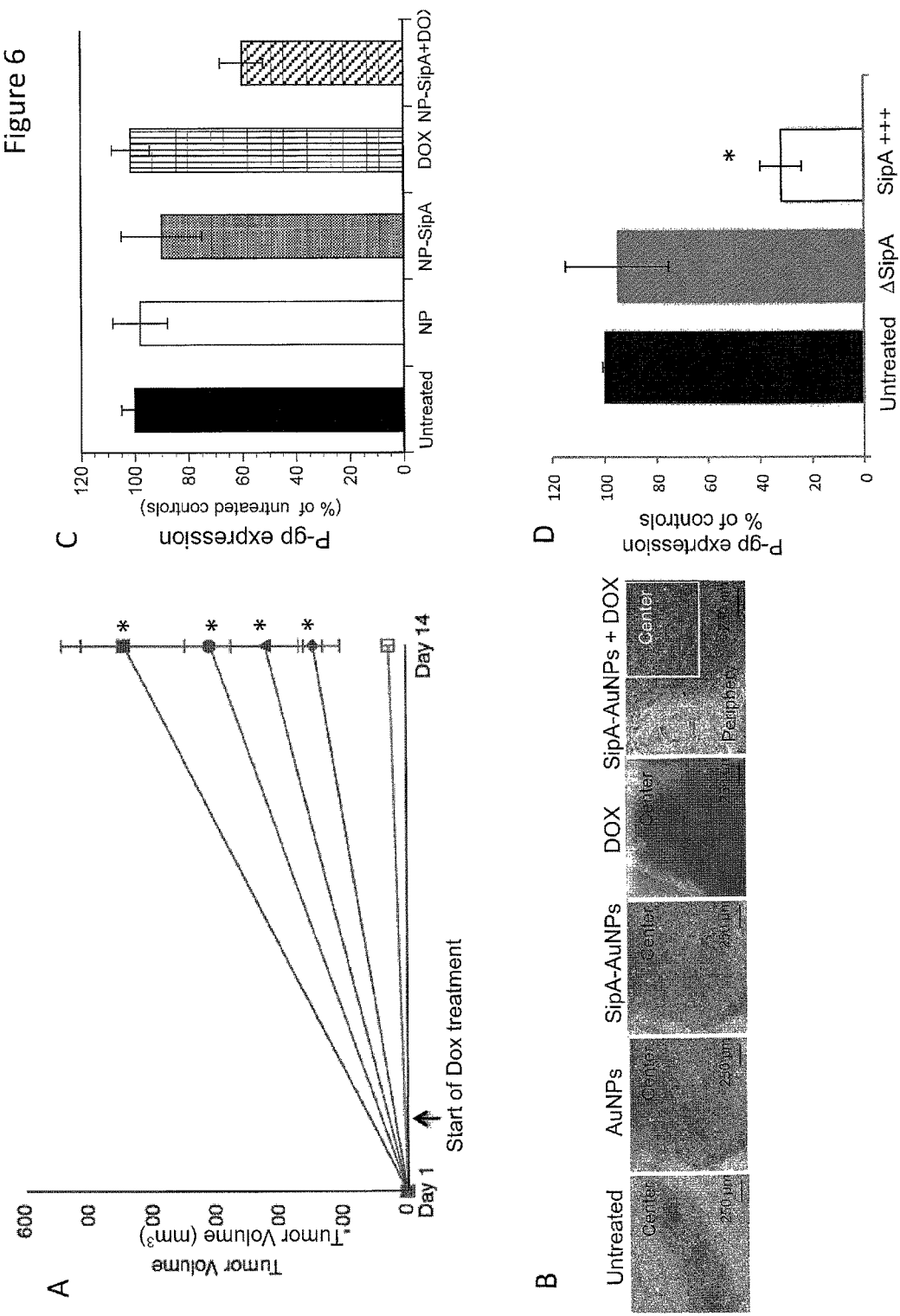
FIG. 6. The combined effects of SipA-AuNPs and exogenous doxorubicin prevent tumor growth. (A) Balb/c mice bearing subcutaneous CT26 tumors (mean tumor volumes of approximately 0.5 mm$^3$) received IP treatments for 15 days as described in the Materials and Methods section. (■) Untreated, (●)AuNP alone, (▲)SipA-AuNPs, (♦) Doxorubicin or (□) SipA-AuNP plus Doxorubicin (DOX). SipA-AuNPs conjugates improve the efficacy of doxorubicin. (*P<0.0001). (B) Accumulation of gold nanoparticles in the tumors shown in (A) was evaluated by SEM and X-ray microanalysis. Color intensity represents tumor penetration. The sections of tumor were imaged for X-ray analysis and X-ray mapping as described in the Materials and Methods section. (C) P-gp expression in the tumors shown in (A) was evaluated by western blot. Tumors were homogenized and lysed. Whole cell lysates were normalized for protein levels and probed for P-gp. Levels of P-gp were quantified by densitometry and presented on the bar cart. Densitometry was performed using ImageJ and results are presented as relative to the untreated cells. (D) Balb/c mice were infected with 10$^7$ CFU of either SL1344 ΔSipA or SL1344 ΔSipA complemented with SipA (ΔSipA/pSipA) for 48 hours, after which the proximal colon was dissected, homogenized and lysed. Whole cell lysates were normalized for protein levels and probed for P-gp. Levels of P-gp were quantified by densitometry and presented on the bar graph. Densitometry was performed using ImageJ and results are presented as relative to the untreated cells. *P<0.0001 (n=6).

As shown in FIG. 6A, the tumor volume following the SipA-AuNP "nanobug"-doxorubicin combination treatment was significantly less than the tumor volumes following either SipA-AuNP or doxorubicin treatment performed alone (P<0.0001).

We found high concentrations of AuNPs in tumors treated with SipA-AuNPs and doxorubicin combination therapy (FIG. 6B), preferentially located in the center of the tumor. Whereas, tumors treated with a tumors either SipA-AuNP or AuNP alone showed a diffuse distribution of the particles. This is consistent with the inventors' observation that P-gp expression is profoundly diminished in tumors that received the SipA-AuNP and DOX combination regiment (FIG. 6C). It is worth noting that the expression of P-gp in tumors that received only the SipA-AuNP treatment was reduced modestly (~10%). It is likely that the different microenvironments encountered by the stable dose SipA-AuNP accounts for these findings. For example, in the SipA-AuNP and DOX combination treatment group, the synergistic effects of P-gp inhibition coupled with the chemotherapeutic drug were marked by profound decreases in both the tumor size and the number of cells, which enabled the SipA-AuNP to further penetrate the tumor and act on cells at an effective concentration. In contrast, the group receiving only the SipA-AuNP regiments, encountered tumors with a high cell proliferation rate, which effectively diluted out the effect of the SipA-AuNPs. Consequently, these tumors did not exhibit modulated P-pg levels.

Consistent with this notion, SipA could modulate the expression of P-gp in healthy murine intestinal epithelium in vivo. Since normal healthy intestinal epithelium display baseline expression of P-gp, the inventors evaluated the colonic expression of P-gp in mice colonized with a *S. Typhimurium* strain that over-expresses SipA (AJK63) compared to mice colonized with an equivalent amount of an isogenic SipA mutant strain (EE633). Under these conditions, the inventors observed a significant decrease in the expression of P-gp in mice that were infected with the SipA over-expressing strain as compared to the SipA mutant strain, the latter of which failed to modulate the expression of P-gp (FIG. 6D). Taken together, these data provide evidence that the SipA protein is responsible for in vivo P-gp down-regulation. the inventors also establish the initial proof of concept that the SipA-AuNPs bacterial mimic, when used in conjunction with the potent cancer chemotherapeutic drug doxorubicin, accumulates in tumors and promotes tumor regression/inhibition with a concomitant decrease in P-gp expression.

Example 7

Nanoparticles Conjugated to SipA

A. Synthesis of the Dithiolated Tetra (Ethylene Glycol) Carboxylic Acid

Figure 8:
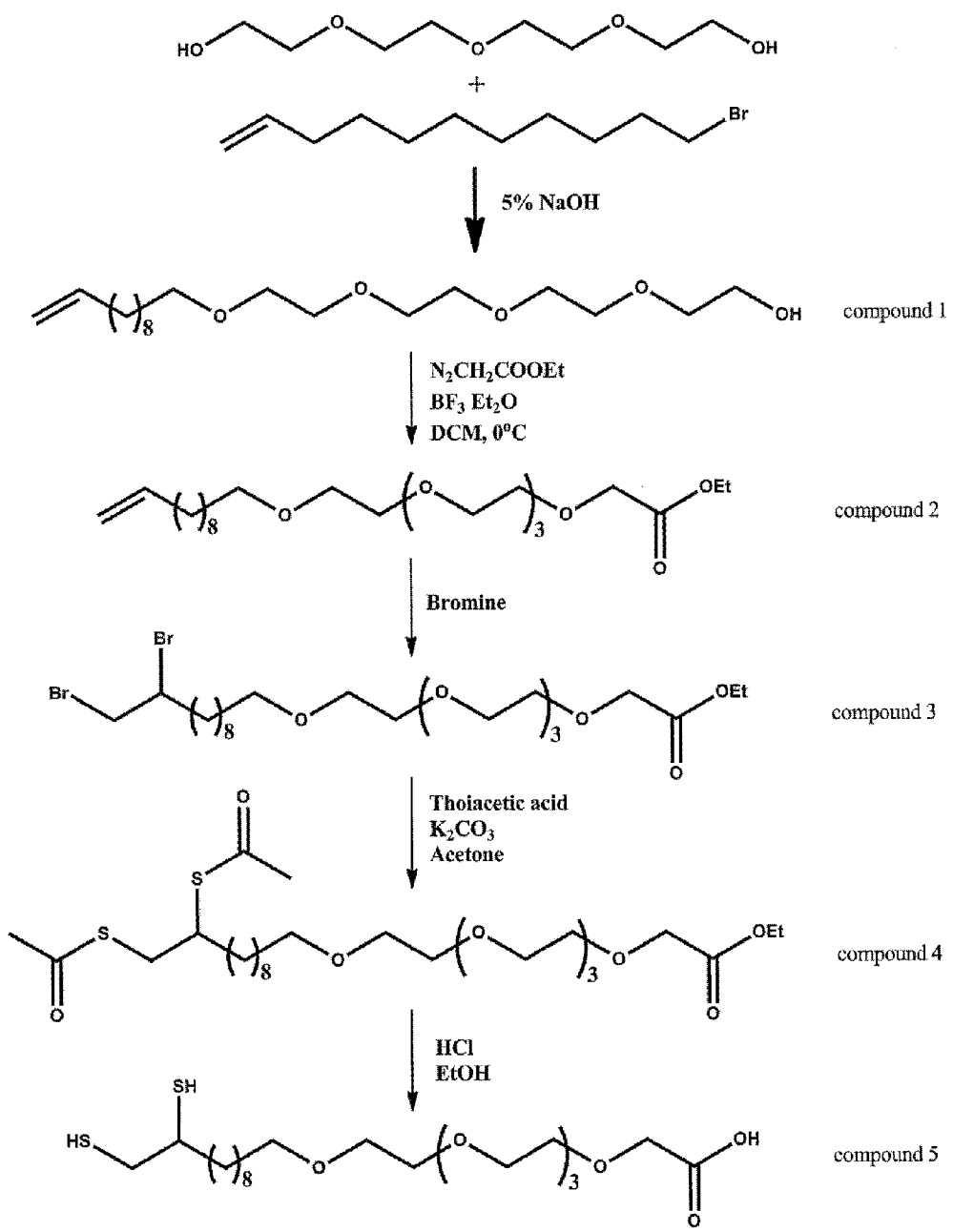
FIG. 8: Scheme of synthesis of the dithiolated tetra (ethylene glycol) carboxylic acid.

The Scheme of synthesis of the dithiolated tetra (ethylene glycol) carboxylic acid is shown in FIG. 8.

Briefly, a mixture of 0.34 mL of 50% aqueous sodium hydroxide (4.3 mmol) and 4.08 g of tetra (ethylene glycol) (21 mmol) was stirred for about 0.5 h in an oil bath at 100° C. under an atmosphere of argon, and then 1.0 g of 11-bromoundec-1-ene (4.3 mmol) was added. After 24 h, the reaction mixture was cooled and extracted six times with hexane. Concentration of the combined hexane portions by rotary evaporation at reduced pressure gave yellow oil containing a mixture of mono- and diethers, according to analysis by 1HNMR spectroscopy. Purification of the oil by chromatography on silica gel (eluant: ethyl acetate) gave 0.98 g of monoether (compound 1): 76% yield; 1H NMR (400 MHz, CDCl,) 1.22-1.27 (m, 10H), 1.29-1.34 (m, 2H), 1.49-1.56 (m, 2H), 1.96-2.02 (m, 2H), 2.73-2.76 (t, 1H), 3.38-3.42 (t, 2H, J=7 Hz), 3.52-3.69 (m, 16H), 4.86-4.97 (m, 2H), 5.71-5.82 (m, 1H). MS (ESI-MS) calcd for C19H38O5 346.50, found 347.2 [M+H]+.

To a solution of Undec-1-en-11-yltetra(ethylene glycol) (compound 1) (1.0 g 2.89 mmol) in dry DCM (6 mL) at 0° C. was added ethyl diazoacetate (0.7 mL, 5.78 mmol) and BF3Et2O (0.29 mmol). After the mixture was stirred for 30 min at 0° C., saturated ammonium chloride (3 mL) was added and the reaction mixture was placed in a separated funnel. The organic phase was collected and the aqueous phase was extracted with DCM (5×150 mL). The combined organic phase was dried over Na2SO4 and concentrated to a yellow oil, which was purified by chromatography using gradient elution hexane (1:1) to ethyl acetate to offered ester. (compound 2) 1H NMR (400 MHz, CDCl,) 1.19-1.22 (m, 13H), 1.26-1.31 (m, 2H), 1.46-1.52 (m, 2H), 1.93-1.98 (m, 2H), 3.35-3.38 (t, 2H, J=7 Hz), 3.52-3.69 (m, 16H), 4.11-4.16 (m, 2H), 4.07 (s, 2H), 4.82-4.93 (m, 2H), 5.69-5.77 (m, 1H). MS (ESI-MS) calcd for C23H44O7 432.31, found 450.2 [M+H3O]+.

To a solution of ester (compound 2) (0.10 g, 0.23 mmol) in dry DCM (10 mL) was added bromine (0.28 mmol) at 0° C. The reaction mixture was stirred at 0° C. for 4 hours at the dark. Thereafter, the reaction mixture was isolated by removal of the solvent using a slight vacuum and a water bath temperature of 30° C. in a rotary evaporator and final drying of the product in vacuum. (compound 3) 1H NMR (400 MHz, CDCl,) 1.22-1.38 (m, 13H), 1.49-1.61 (m, 4H), 1.71-1.80 (m, 2H), 3.42-3.47 (t, 2H, J=7 Hz), 3.58-3.77 (m, 17H), 3.81-4.87 (m, 1H), 4.17 (s, 2H), 4.19-4.22 (m, 3H). MS (ESI-MS) calcd for C23H44Br2O7 592.40, found 615.2 [M+Na]+.

A solution of dibromine (compound 3) (100 mg, 0.17 mmol) and K2CO3 (117 mg, 0.85 mmol) in acetone (10 mL) was added thioacetic acid (129 mg, 1.7 mmol). The reaction mixture was stirred at room temperature overnight. (compound 4) 1H NMR (400 MHz, CDCl,) 1.09-1.35 (m, 13H), 1.48-1.68 (m, 4H), 1.93-2.01 (m, 2H), 2.32 (s, 6H), 3.08-3.28 (m, 1H), 3.39-3.50 (m, 3H), 3.55-3.78 (m, 17H), 4.15 (s, 2H), 4.18-4.24 (m, 2H). MS (ESI-MS) calcd for C27H50O9S2 582.81, found 621.3 [M+K]+.

The solution of diactyl-OEt (compound 4) in ethyl alcohol was then added concentrated hydrochloric acid and stirred overnight to provide free thiol compound. (compound 5) 1H NMR (400 MHz, CDCl,) 1.18-1.38 (m, 10H), 1.49-1.61 (m, 8H), 2.72-2.98 (m, 3H), 3.36-3.42 (t, 2H, J=7 Hz), 3.55-3.77 (m, 16H), 4.17 (s, 2H). MS (ESI-MS) calcd for C21H42O7S2 470.68, found 471.3 [M+H]+.

B. Determining the Ratio of AuNP to Surface Conjugated SipA Proteins.

Figure 9:
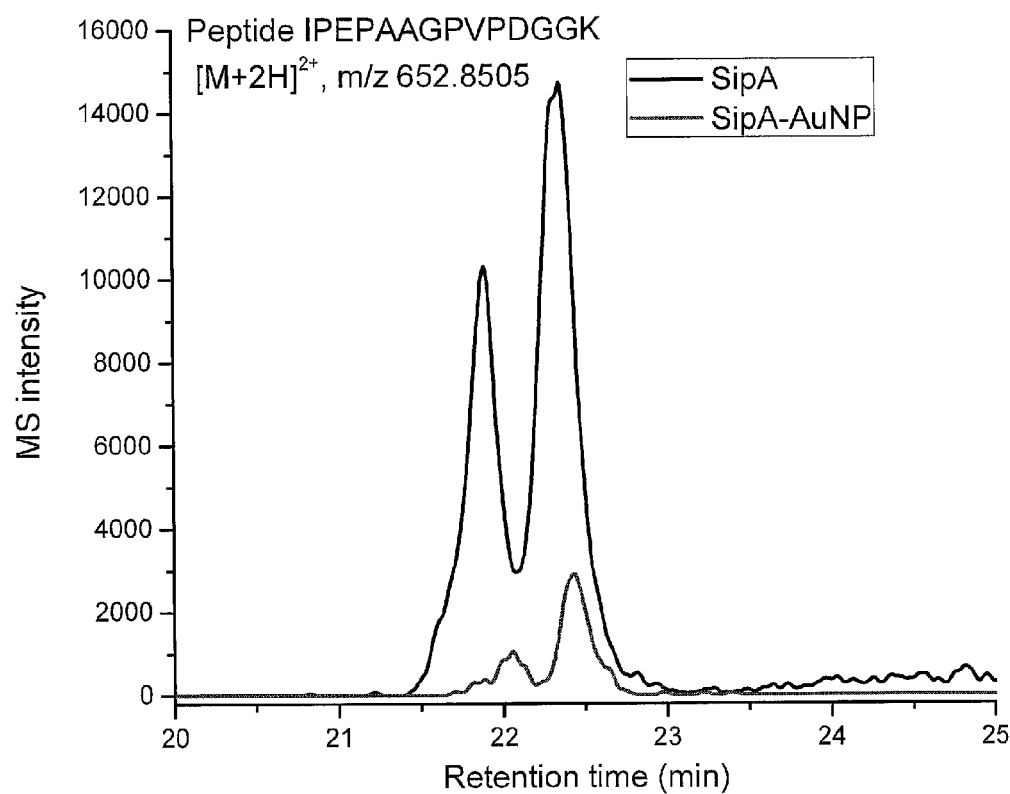
FIG. 9: The extracted ion chromatograph (EIC) peaks for peptide IPEPAAGPVPDGGK from the Sip A and SipA-AuNP samples.

To determine the ratio of AuNP to corona SipA proteins, the inventors exposed the SipA-AuNP (7.2 pmoles) sample to sodium cyanide, which decomposes the gold particle core. This afforded solution was then dialyzed for one day using a Slide-A-Lyzer MINI dialysis unit (MW=10,000), and thereafter concentrated to 45 µl. This sample and the same volume Sip A only (45 µl, 540.7 µg/ml) sample are trypsin digested and measured with an Agilent Q-TOF 6538 mass spectrometer coupled with an Agilent HPLC 1200. Peptide IPEPAAGPVPDGGK ([M+2H]2+, m/z 652.8505) from the SipA protein is identified through MS/MS spectral match, and chosen for as surrogate for protein quantification. The extracted ion chromatograph (EIC) peaks for this peptide from the aforementioned two samples are integrated and compared. (FIG. 9). The ratio protein only/protein from SipA-AuNP is 7.5 based on the integrated areas. Thus the total amount of SipA from SipA-AuNP can be determined by the following equation:

(45 µl×540.7 µg/ml)/7.5=3.24 µg or 3.24 µg/74,000 g/mol (MW of SipA)=43.8 pmoles The ratio of AuNP and conjugated SipA was thus estimated to be 1:6 (7.2 pmols vs. 43.8 pmols).

REFERENCES CITED ABOVE IN "BACKGROUND OF THE INVENTION" and "BRIEF DESCRIPTION OF THE INVENTION"

1. B. Wiemann, C. O. Starnes, Coley's toxins, tumor necrosis factor and cancer research: a historical perspective. *Pharmacol Ther* 64, 529 (1994).
2. K. B. Low et al., Construction of VNP20009: a novel, genetically stable antibiotic-sensitive strain of tumor-targeting *Salmonella* for parenteral administration in humans. *Methods Mol Med* 90, 47 (2004).
3. R. Krishna, L. D. Mayer, Modulation of P-glycoprotein (PGP) mediated multidrug resistance (MDR) using chemosensitizers: recent advances in the design of selective MDR modulators. *Curr Med Chem Anticancer Agents* 1, 163 (August, 2001).
4. R. L. Juliano, V. Ling, A surface glycoprotein modulating drug permeability in Chinese hamster ovary cell mutants. *Biochimica et biophysica acta* 455, 152 (Nov. 11, 1976).
5. D. Siccardi, K. L. Mumy, D. M. Wall, J. D. Bien, B. A. McCormick, *Salmonella enterica* serovar *Typhimurium* modulates P-glycoprotein in the intestinal epithelium. *Am J Physiol Gastrointest Liver Physiol* 294, G1392 (June, 2008).
6. L. A. Diaz, Jr. et al., Pharmacologic and toxicologic evaluation of C. novyi-NT spores. *Toxicol Sci* 88, 562 (December, 2005).
7. J. M. Pawelek, K. B. Low, D. Bermudes, Tumor-targeted *Salmonella* as a novel anticancer vector. *Cancer Res* 57, 4537 (Oct. 15, 1997).
8. R. D. Baird, S. B. Kaye, Drug resistance reversal—are the inventors getting closer? *Eur J Cancer* 39, 2450 (November, 2003).
9. I. M. Ghobrial, T. E. Witzig, A. A. Adjei, Targeting apoptosis pathways in cancer therapy. *CA Cancer J Clin* 55, 178 (May-June, 2005).
10. L. Davies, D. Spiller, M. R. White, I. Grierson, L. Paraoan, PERP expression stabilizes active p53 via modulation of p53-MDM2 interaction in uveal melanoma cells. *Cell Death Dis* 2, e136 (2011).
11. A. J. Levine, p53, the cellular gatekeeper for growth and division. *Cell* 88, 323 (Feb. 7, 1997).
12. B. Vogelstein, D. Lane, A. J. Levine, Surfing the p53 network. *Nature* 408, 307 (Nov. 16, 2000).
13. D. M. Wall et al., Identification of the *Salmonella enterica* serotype *typhimurium* SipA domain responsible for inducing neutrophil recruitment across the intestinal epithelium. *Cell Microbiol* 9, 2299 (September, 2007).
14. C. A. Lee et al., A secreted *Salmonella* protein induces a proinflammatory response in epithelial cells, which promotes neutrophil migration. *Proceedings of the National Academy of Sciences of the United States of America* 97, 12283 (Oct. 24, 2000).
15. V. G. Beaudry et al., Loss of the p53/p63 regulated desmosomal protein Perp promotes tumorigenesis. *PLoS genetics* 6, e1001168 (October, 2010).

REFERENCES CITED ABOVE IN "DETAILED DESCRIPTION OF THE INVENTION" AND "EXPERIMENTAL"

1. B. Wiemann, C. O. Starnes, Coley's toxins, tumor necrosis factor and cancer research: a historical perspective. *Pharmacol Ther* 64, 529 (1994).
2. J. M. Pawelek, K. B. Low, D. Bermudes, Tumor-targeted *Salmonella* as a novel anticancer vector. *Cancer Res* 57, 4537 (Oct. 15, 1997).
3. K. B. Low et al., Construction of VNP20009: a novel, genetically stable antibiotic-sensitive strain of tumor-targeting *Salmonella* for parenteral administration in humans. *Methods Mol Med* 90, 47 (2004).
4. J. E. Galan, Molecular and cellular bases of *Salmonella* entry into host cells. *Curr Top Microbiol Immunol* 209, 43 (1996).
5. A. Haraga, M. B. Ohlson, S. I. Miller, Salmonellae interplay with host cells. *Nature reviews. Microbiology* 6, 53 (January, 2008).
6. R. Krishna, L. D. Mayer, Modulation of P-glycoprotein (PGP) mediated multidrug resistance (MDR) using chemosensitizers: recent advances in the design of selective MDR modulators. *Curr Med Chem Anticancer Agents* 1, 163 (August, 2001).
7. R. L. Juliano, V. Ling, A surface glycoprotein modulating drug permeability in Chinese hamster ovary cell mutants. *Biochimica et biophysica acta* 455, 152 (Nov. 11, 1976).
8. D. Siccardi, K. L. Mumy, D. M. Wall, J. D. Bien, B. A. McCormick, *Salmonella enterica* serovar *Typhimurium* modulates P-glycoprotein in the intestinal epithelium. *Am J Physiol Gastrointest Liver Physiol* 294, G1392 (June, 2008).
9. D. M. Wall et al., Identification of the *Salmonella enterica* serotype *typhimurium* SipA domain responsible for inducing neutrophil recruitment across the intestinal epithelium. *Cell Microbiol* 9, 2299 (September, 2007).
10. I. Mantovani et al., Caspase-dependent cleavage of 170-kDa P-glycoprotein during apoptosis of human T-lymphoblastoid CEM cells. *J Cell Physiol* 207, 836 (June, 2006).
11. C. V. Srikanth et al., *Salmonella* pathogenesis and processing of secreted effectors by caspase-3. *Science* 330, 390 (Oct. 15, 2010).
12. S. Rana, A. Bajaj, R. Mout, V. M. Rotello, Monolayer coated gold nanoparticles for delivery applications. *Adv Drug Deliv Rev* 64, 200 (February, 2012).

13. G. Han, P. Ghosh, V. M. Rotello, Functionalized gold nanoparticles for drug delivery. *Nanomedicine (Lond)* 2, 113 (February, 2007).
14. R. Hong et al., Control of protein structure and function through surface recognition by tailored nanoparticle scaffolds. *J Am Chem Soc* 126, 739 (Jan. 28, 2004).
15. M. Wang, M. Thanou, Targeting nanoparticles to cancer. *Pharmacol Res* 62, 90 (August, 2010).
16. T. Kubota et al., Reduced HGF expression in subcutaneous CT26 tumor genetically modified to secrete NK4 and its possible relation with antitumor effects. *Cancer Sci* 95, 321 (April, 2004).
17. D. Wang et al., Antitumor activity and immune response induction of a dual agonist of Toll-like receptors 7 and 8. *Mol Cancer Ther* 9, 1788 (June, 2010).
18. R. W. Johnstone, A. A. Ruefli, M. J. Smyth, Multiple physiological functions for multidrug transporter P-glycoprotein? *Trends in biochemical sciences* 25, 1 (January, 2000).
19. G. T. Ho, F. M. Moodie, J. Satsangi, Multidrug resistance 1 gene (P-glycoprotein 170): an important determinant in gastrointestinal disease? *Gut* 52, 759 (May, 2003).
20. T. Fojo, S. Bates, Strategies for reversing drug resistance. *Oncogene* 22, 7512 (Oct. 20, 2003).
21. R. D. Baird, S. B. Kaye, Drug resistance reversal—are the inventors getting closer? *Eur J Cancer* 39, 2450 (November, 2003).
22. C. A. Lee et al., A secreted *Salmonella* protein induces a proinflammatory response in epithelial cells, which promotes neutrophil migration. *Proceedings of the National Academy of Sciences of the United States of America* 97, 12283 (Oct. 24, 2000).

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A method comprising administering to a mammalian cell a composition comprising purified SipA, wherein said SipA is in an amount that is effective in one or more of
    a) reducing the level of expression of P-gp in said cell,
    b) reducing the level of un-cleaved P-gp in said cell, and
    c) increasing the level of expression of PERP in said cell, wherein said cell is a cancer cell in vitro and said purified SipA is fused to human influenza hemagglutinin (HA).

2. A method comprising administering to a mammalian cell a composition comprising purified SipA, wherein said SipA is in an amount that is effective in one or more of
    a) reducing the level of expression of P-gp in said cell,
    b) reducing the level of un-cleaved P-gp in said cell, and
    c) increasing the level of expression of PERP in said cell, wherein said cell is a cancer cell in vitro and said purified SipA is conjugated to a nanoparticle.

* * * * *